US012307561B2

(12) United States Patent
Ishigaki et al.

(10) Patent No.: US 12,307,561 B2
(45) Date of Patent: May 20, 2025

(54) DISPLAY CONTROL APPARATUS, DISPLAY CONTROL METHOD, AND DISPLAY CONTROL PROGRAM

(71) Applicant: FUJIFILM Corporation, Tokyo (JP)

(72) Inventors: Junichi Ishigaki, Tokyo (JP); Eiichi Imamichi, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 17/822,040

(22) Filed: Aug. 24, 2022

(65) Prior Publication Data
US 2022/0405992 A1 Dec. 22, 2022

Related U.S. Application Data

(63) Continuation of application No. PCT/JP2021/006421, filed on Feb. 19, 2021.

(30) Foreign Application Priority Data

Mar. 9, 2020 (JP) ................................ 2020-040358

(51) Int. Cl.
*G06T 11/20* (2006.01)
*G06F 3/04855* (2022.01)

(52) U.S. Cl.
CPC ........ *G06T 11/203* (2013.01); *G06F 3/04855* (2013.01); *G06T 2200/24* (2013.01); *G06T 2210/41* (2013.01)

(58) Field of Classification Search
None
See application file for complete search history.

(56) References Cited

U.S. PATENT DOCUMENTS

2005/0171430 A1 8/2005 Zhang et al.
2010/0141654 A1\* 6/2010 Neemuchwala ....... A61B 8/483
345/427

(Continued)

FOREIGN PATENT DOCUMENTS

JP 2004-173910 A 6/2004
JP 2008-501436 A 1/2008

(Continued)

OTHER PUBLICATIONS

International Search Report issued in PCT/JP2021/006421; mailed Apr. 13, 2021.

(Continued)

*Primary Examiner* — Andre L Matthews
(74) *Attorney, Agent, or Firm* — Studebaker Brackett PLLC

(57) ABSTRACT

A CPU displays a slider bar and a slider that are for designating a tomographic position, and displays a tomographic image corresponding to a designated tomographic position. For each of one or more specific tomographic images with additional information that is set to be added on a tomographic-image by tomographic-image basis, the CPU displays a marking representing the additional information at a position corresponding to a tomographic position of the specific tomographic image on the slider bar. The CPU receives a specific display instruction to display, among a plurality of tomographic images, only the specific tomographic images that are on either side of the slider bar in the depth direction with respect to a reference that is a current position designated by the slider. The CPU then displays only the specific tomographic images in an order according to the depth direction, and displays the markings representing the additional information added to the respective spe- (Continued)

cific tomographic images in an emphasized manner in the order according to the depth direction.

17 Claims, 15 Drawing Sheets

(56) References Cited

U.S. PATENT DOCUMENTS

| | | | |
|---|---|---|---|
| 2014/0229890 A1* | 8/2014 | Tokunaga | A61B 6/465 |
| | | | 715/786 |
| 2015/0052471 A1 | 2/2015 | Chen et al. | |
| 2016/0051215 A1 | 2/2016 | Chen et al. | |
| 2016/0063917 A1 | 3/2016 | Kondo | |
| 2017/0300625 A1* | 10/2017 | Venon | G16H 30/20 |
| 2018/0218672 A1 | 8/2018 | Kondo | |
| 2020/0121393 A1* | 4/2020 | Nakamura | G06T 19/003 |
| 2020/0279652 A1* | 9/2020 | Nenoki | G16H 50/20 |

FOREIGN PATENT DOCUMENTS

| | | |
|---|---|---|
| JP | 2015-506794 A | 3/2015 |
| JP | 2015-171437 A | 10/2015 |
| JP | 2016-510669 A | 4/2016 |
| JP | 2016-106699 A | 6/2016 |
| JP | 2016-174656 A | 10/2016 |
| JP | 2019-103944 A | 6/2019 |
| WO | 2014/203438 A1 | 12/2014 |

OTHER PUBLICATIONS

International Preliminary Report on Patentability (Chapter I) and Written Opinion of the International Searching Authority issued in PCT/JP2021/006421; issued Sep. 6, 2022.

An Office Action; "Notice of Reasons for Refusal," mailed by the Japanese Patent Office on Jul. 11, 2023, which corresponds to Japanese Patent Application No. 2022-505887 and is related to U.S. Appl. No. 17/822,040; with English language translation.

* cited by examiner

DISPLAY CONTROL APPARATUS, DISPLAY CONTROL METHOD, AND DISPLAY CONTROL PROGRAM

CROSS-REFERENCE TO RELATED APPLICATION

This application is a continuation application of International Application No. PCT/JP2021/006421, filed Feb. 19, 2021, the disclosure of which is incorporated herein by reference in its entirety. Further, this application claims priority from Japanese Patent Application No. 2020-040358 filed on Mar. 9, 2020, the disclosure of which is incorporated herein by reference in its entirety.

BACKGROUND

1. Technical Field

The present disclosure relates to a display control apparatus, a display control method, and a display control program.

2. Description of the Related Art

In recent years, image-based diagnosis has been performed using a three-dimensional medical image captured with imaging apparatuses such as a computed tomography (CT) apparatus and a magnetic resonance imaging (MRI) apparatus. Such a three-dimensional image includes tomographic images at a plurality of tomographic positions different from each other. In image-based diagnosis performed by a doctor using the three-dimensional image, the plurality of tomographic images are switched between and displayed.

A technique for displaying a slider bar for designating a tomographic position corresponding to each of a plurality of tomographic images has been proposed (see JP2004-173910A) as a technique for switching between and displaying the plurality of tomographic images. In this technique, a slider is displayed on the slider bar. A user moves the slider to designate a tomographic position. Then, a tomographic image corresponding to the designated tomographic position is displayed. In this technique, for example, at a tomographic position corresponding to a tomographic image that includes a result (hereinafter, referred to as a "computer diagnosis result") of image-based diagnosis performed by a computer such as an abnormal shadow candidate, a marking indicating inclusion of the computer diagnosis result is also displayed.

A technique for displaying all tomographic images included in a set tomographic position range in a forward order one by one has also been proposed (see WO2014/203438A).

SUMMARY

In a method for designating the tomographic position using the slider bar as in the technique described in JP2004-173910A, a user may have difficulty in observing a tomographic image with additional information such as the computer diagnosis result. Such an issue is problematic particularly when there are many tomographic images with the additional information. The reason for this is that when there are many tomographic images with the additional information, a plurality of markings corresponding to the respective tomographic images may be close to each other over the slider bar. In this case, if the position for a tomographic image without any marking is included between the markings that are close to each other, the user may mistakenly designate the position of the tomographic image without any marking, despite an intention to designate a position of a tomographic image with the marking using the slider bar. Thus, in the method for designating the tomographic position using the slider bar, the user may have difficulty in observing the tomographic image with the additional information.

The technique described in WO2014/203438A is merely a technique for displaying all tomographic images in a forward order regardless of whether or not the additional information is present, and thus does not give any consideration to a method for observing a tomographic image with the additional information.

The present disclosure is made in view of the circumstances described above, and provides a display control apparatus, a display control method, and a display control program capable of making it easier to observe a tomographic image with additional information.

A display control apparatus according to a first aspect of the present disclosure is a display control apparatus including at least one processor. The processor performs control to display a designation object for designating a tomographic position corresponding to each of a plurality of tomographic images for medical use obtained through imaging of a subject; display a tomographic image corresponding to a tomographic position designated by the designation object; display, for each of one or more specific tomographic images with additional information that is set to be added on a tomographic-image by tomographic-image basis, a marking representing the additional information at a position corresponding to a tomographic position of the specific tomographic image in a depth direction of the designation object; receive a specific display instruction to display, among the plurality of tomographic images, only the specific tomographic images that are on either side of the designation object in the depth direction with respect to a reference that is a current position designated by the designation object; display, in response to receipt of the specific display instruction, only the specific tomographic images in an order according to the depth direction; and display, in response to only the specific tomographic images being displayed in the order according to the depth direction, the markings representing the additional information added to the respective specific tomographic images in an emphasized manner in the order according to the depth direction.

In addition, a display control apparatus according to a second aspect of the present disclosure is the display control apparatus according to the first aspect in which the designation object includes a slider bar.

In addition, a display control apparatus according to a third aspect of the present disclosure is the display control apparatus according to the first aspect in which the designation object includes a schema.

In addition, a display control apparatus according to a fourth aspect of the present disclosure is the display control apparatus according to any one of the first to third aspects in which the additional information includes a plurality of kinds of additional information, and the processor is capable of receiving, as the specific display instruction, a specific display instruction including designation of a kind of the additional information, and performs control to display, in response to receipt of the specific display instruction in which the kind of the additional information is designated, only the specific tomographic images with the additional information of the designated kind in the order according to the depth direction.

In addition, a display control apparatus according to a fifth aspect of the present disclosure is the display control apparatus according to the fourth aspect in which the plurality of kinds include at least one of user-added additional information added by a user or computer-added additional information added by a computer.

In addition, a display control apparatus according to a sixth aspect of the present disclosure is the display control apparatus according to the fourth or fifth aspect in which the processor is capable of receiving, as the specific display instruction, a specific display instruction not including designation of a kind of the additional information, and performs control to display, in response to receipt of the specific display instruction, all the specific tomographic images with the additional information in the order according to the depth direction irrespective of the kinds.

In addition, a display control apparatus according to a seventh aspect of the present disclosure is the display control apparatus according to any one of the first to sixth aspects in which the order according to the depth direction includes a first order corresponding to a forward direction set in advance in the depth direction and a second order corresponding to a reverse direction opposite to the forward direction, and the processor is capable of receiving, as the specific display instruction, a specific display instruction in which either the first order or the second order is designated.

In addition, a display control apparatus according to an eighth aspect of the present disclosure is the display control apparatus according to any one of the first to seventh aspects in which the processor performs control to display an instruction button for giving the specific display instruction.

In addition, a display control apparatus according to a ninth aspect of the present disclosure is the display control apparatus according to any one of the first to eighth aspects in which the processor receives the specific display instruction input by an instruction input device.

In addition, the display control apparatus according to a tenth aspect of the present disclosure is the display control apparatus according to any one of the first to ninth aspects in which the processor performs control to display the total number of specific tomographic images at a position different from a position of the designation object.

In addition, a display control apparatus according to an eleventh aspect of the present disclosure is the display control apparatus according to any one of the first to tenth aspects in which the processor performs control to display the total number of specific tomographic images included in the plurality of tomographic images and order information indicating what number, in the order according to the depth direction, one of the specific tomographic images that is currently displayed based on the specific display instruction is.

In addition, a display control apparatus according to a twelfth aspect of the present disclosure is the display control apparatus according to the eleventh aspect in which the additional information includes a plurality of kinds of additional information, and the processor performs control to display the total number and the order information for each of the plurality of kinds.

In addition, a display control apparatus according to a thirteenth aspect of the present disclosure is the display control apparatus according to the twelfth aspect in which the processor is capable of receiving, as the specific display instruction, a specific display instruction including designation of a kind of the additional information, and performs control to selectively display the total number and the order information in accordance with the designated kind.

In addition, a display control apparatus according to a fourteenth aspect of the present disclosure is the display control apparatus according to any one of the first to thirteenth aspects in which the additional information includes computer-added additional information added by a computer, and the processor receives an input for switching between displaying and hiding of the computer-added additional information, and performs control to switch between displaying and hiding of a marking representing the computer-added additional information in accordance with the received input.

In addition, a display control apparatus according to a fifteenth aspect of the present disclosure is the display control apparatus according to the fourteenth aspect in which the processor performs control to display, for a tomographic image with the computer-added additional information, the computer-added additional information over the tomographic image, and performs control to switch between displaying and hiding of both the marking representing the computer-added additional information and the computer-added additional information over the tomographic image in accordance with the received input.

In addition, a display control apparatus according to a sixteenth aspect of the present disclosure is the display control apparatus according to any one of the first to fifteenth aspects in which the additional information includes an outline of a region of interest in the tomographic image, and the processor performs control to display, in a case where the outline of the region of interest is added to the tomographic image corresponding to the designated tomographic position, the outline of the region of interest over the tomographic image, and performs control to further display an outline of the region of interest added to any of other tomographic images in which a region of interest identical to the region of interest being displayed is detected.

In addition, a display control apparatus according to a seventeenth aspect of the present disclosure is the display control apparatus according to the sixteenth aspect in which the processor performs control to display a largest outline among outlines of the region of interest added to the other tomographic images.

In addition, a display control method according to an eighteenth aspect of the present disclosure is a display control method in which a processor, which a display control apparatus includes, performs a process of performing control to display a designation object for designating a tomographic position corresponding to each of a plurality of tomographic images for medical use obtained through imaging of a subject; display a tomographic image corresponding to a tomographic position designated by the designation object; display, for each of one or more specific tomographic images with additional information that is set to be added on a tomographic-image by tomographic-image basis, a marking representing the additional information at a position corresponding to a tomographic position of the specific tomographic image in a depth direction of the designation object; receive a specific display instruction to display, among the plurality of tomographic images, only the specific tomographic images that are on either side of the designation object in the depth direction with respect to a reference that is a current position designated by the designation object; display, in response to receipt of the specific display instruction, only the specific tomographic images in an order according to the depth direction; and display, in response to only the specific tomographic images being displayed in the order according to the depth direction, the markings representing the additional information added to the respective specific tomographic images in an emphasized manner in the order according to the depth direction.

In addition, a display control program according to a nineteenth aspect of the present disclosure causes a processor, which a display control apparatus includes, to perform a process for performing control to display a designation object for designating a tomographic position corresponding to each of a plurality of tomographic images for medical use obtained through imaging of a subject; display a tomographic image corresponding to a tomographic position designated by the designation object; display, for each of one or more specific tomographic images with additional information that is set to be added on a tomographic-image by tomographic-image basis, a marking representing the additional information at a position corresponding to a tomographic position of the specific tomographic image in a depth direction of the designation object; receive a specific display instruction to display, among the plurality of tomographic images, only the specific tomographic images that are on either side of the designation object in the depth direction with respect to a reference that is a current position designated by the designation object; display, in response to receipt of the specific display instruction, only the specific tomographic images in an order according to the depth direction; and display, in response to only the specific tomographic images being displayed in the order according to the depth direction, the markings representing the additional information added to the respective specific tomographic images in an emphasized manner in the order according to the depth direction.

The present disclosure can make it easier to observe a tomographic image with additional information.

BRIEF DESCRIPTION OF THE DRAWINGS

Exemplary embodiments according to the technique of the present disclosure will be described in detail based on the following figures, wherein.

DETAILED DESCRIPTION

An embodiment for implementing a technique of the present disclosure will be described in detail below with reference to the drawings.

Figure 1:
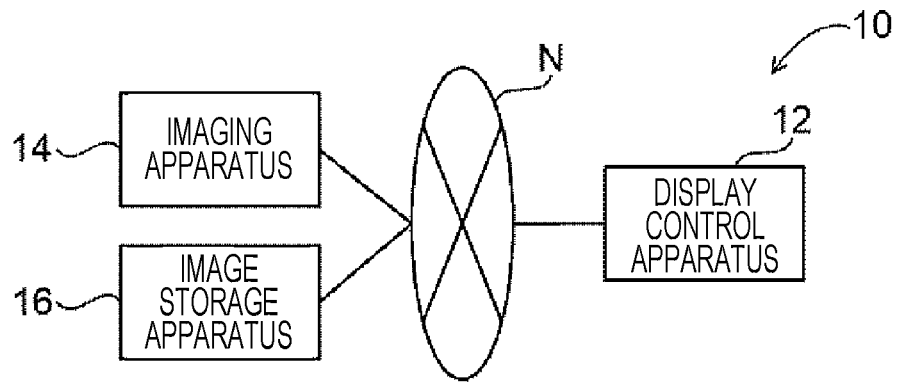
FIG. 1 is a block diagram illustrating an example of a configuration of a diagnosis assistance system.

First, a configuration of a diagnosis assistance system 10 according to the present embodiment will be described with reference to FIG. 1. As illustrated in FIG. 1, the diagnosis assistance system 10 includes a display control apparatus 12, an imaging apparatus 14, and an image storage apparatus 16. The display control apparatus 12, the imaging apparatus 14, and the image storage apparatus 16 are connected to a network N and can communicate with each other via the network N.

The imaging apparatus 14 is an apparatus that images a diagnosis-target part of a subject to generate a three-dimensional medical image representing the part. The three-dimensional medical image captured by the imaging apparatus 14 includes a plurality of tomographic images. In the present embodiment, an example will be described in which a CT apparatus is used as the imaging apparatus 14. However, the imaging apparatus 14 is not limited to this. For example, an apparatus that generates a three-dimensional medical image other than a CT apparatus, such as an MRI apparatus or a positron emission tomography (PET) apparatus, may be used as the imaging apparatus 14. In the present embodiment, an example will be described in which tomographic images of axial cross-sections are used as the tomographic images constituting the three-dimensional medical image. However, the tomographic images are not limited to these. As the tomographic images constituting the three-dimensional medical image, tomographic images of cross-sections other than the axial cross-sections, such as sagittal cross-sections and coronal cross-sections, may be used.

The image storage apparatus 16 is a computer that stores and manages a medical image, and includes a storage device or the like in which the medical image is stored. The image storage apparatus 16 transmits and receives a medical image generated by the imaging apparatus 14 to and from the display control apparatus 12 and the imaging apparatus 14, respectively, via the network N. A storage format of the medical image and communication performed between the apparatuses via the network N are based on a predetermined protocol such as Digital Imaging and Communication in Medicine (DICOM).

A hardware configuration of the display control apparatus 12 according to the present embodiment will be described next with reference to FIG. 2. Examples of the display control apparatus 12 include a personal computer, a server computer, or the like. The display control apparatus 12 may be a cloud server or the like.

Figure 2:
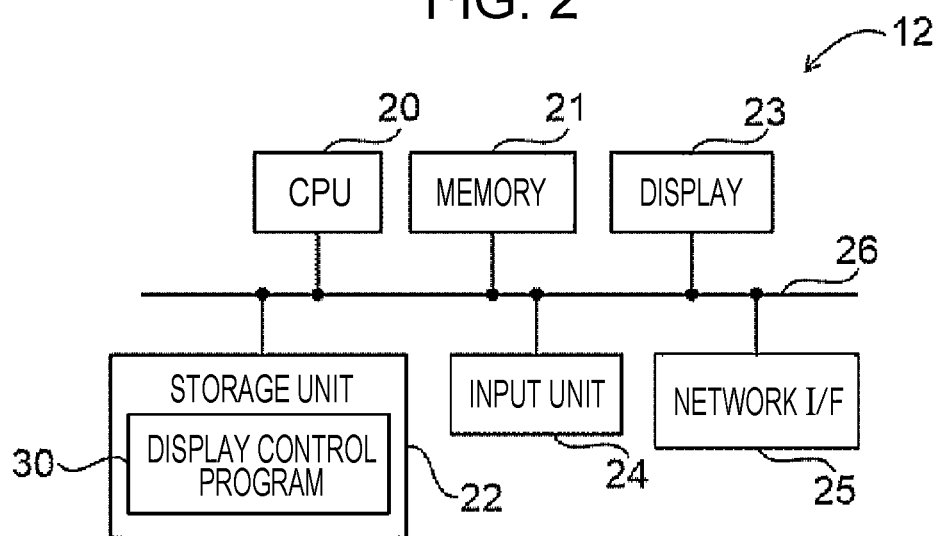
FIG. 2 is a block diagram illustrating an example of a hardware configuration of a display control apparatus.

As illustrated in FIG. 2, the display control apparatus 12 includes a central processing unit (CPU) 20, a memory 21 serving as a temporary storage area, and a storage unit 22 that is nonvolatile. The display control apparatus 12 also includes a display 23 such as a liquid crystal display, an input unit 24 such as a keyboard and a mouse, and a network interface (I/F) 25 connected to the network N. The display 23 and the input unit 24 may be integrated into a touch panel display. The input unit 24 in the present embodiment is an example of an instruction input device in the present disclosure. The instruction input device according to the present disclosure may be included in the display control apparatus 12 as in the present embodiment, or may be a device external to the display control apparatus 12 unlike the present embodiment. The CPU 20, the memory 21, the storage unit 22, the display 23, the input unit 24, and the network I/F 25 are connected to a bus 26.

The storage unit 22 is implemented by a hard disk drive (HDD), a solid state drive (SSD), a flash memory, or the like. A display control program 30 is stored in the storage unit 22 that serves as a storage medium. The CPU 20 reads out the display control program 30 from the storage unit 22, loads the display control program 30 into the memory 21, and executes the loaded display control program 30.

Figure 3:
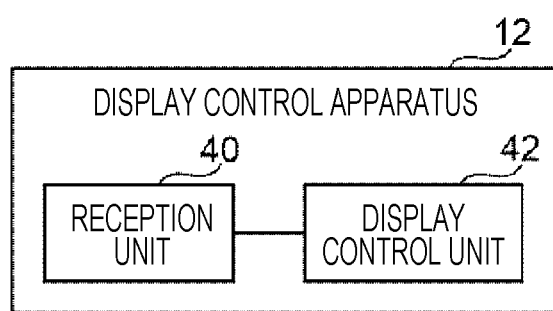
FIG. 3 is a block diagram illustrating an example of a functional configuration of the display control apparatus.

A functional configuration of the display control apparatus 12 according to the present embodiment will be described next with reference to FIG. 3. As illustrated in FIG. 3, the display control apparatus 12 includes a reception unit 40 and a display control unit 42. The CPU 20 executes the display control program 30 to function as the reception unit 40 and the display control unit 42.

The reception unit 40 receives various instructions input by a user via the input unit 24. Details of the various instructions given by the user will be described later.

Figure 4:
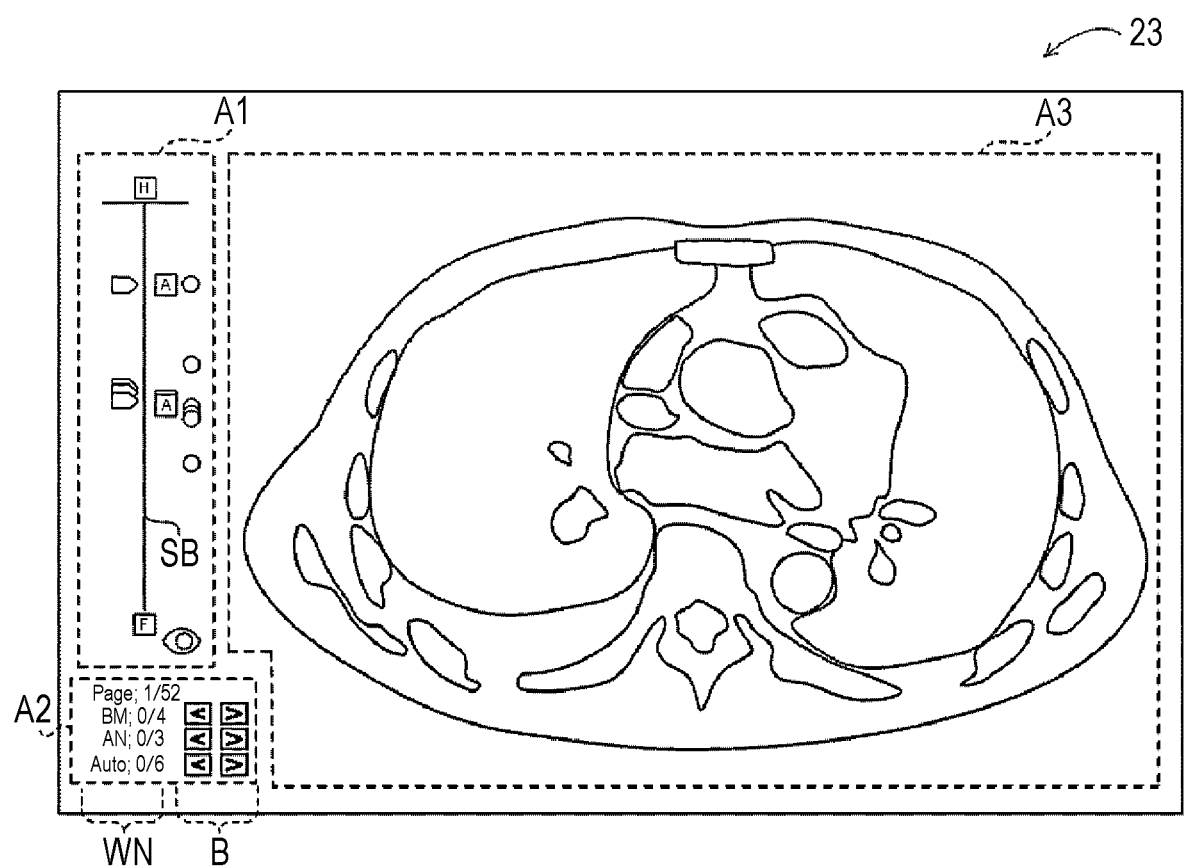
FIG. 4 is a diagram illustrating an example of a screen displaying a slider bar, display information, scroll buttons, and a tomographic image.

As illustrated in FIG. 4, the display control unit 42 performs control to display, on the display 23, a slider bar SB for designating a tomographic position corresponding to each of a plurality of tomographic images for medical use obtained through imaging of a subject and a tomographic image corresponding to the designated tomographic position. The slider bar SB and a slider SD (described later) in the present embodiment are an example of a designation object for designating a tomographic position corresponding to each of a plurality of tomographic images in the present disclosure.

As illustrated in FIG. 4, the display control unit 42 performs control to display, on the display 23, display information WN indicating what number the displayed tomographic image is and scroll buttons B for switching the displayed tomographic image. These plurality of tomographic images for medical use obtained through imaging of the subject are a group of tomographic images constituting a three-dimensional medical image designated as a display target from among the three-dimensional medical images stored in the image storage apparatus 16. As illustrated in FIG. 4, the screen displayed on the display 23 includes a display region A1 in which the slider bar SB is displayed, a display region A2 in which the display information WN and the scroll buttons B are displayed, and a display region A3 in which a tomographic image is displayed. The scroll buttons B in the present embodiment are an example of an instruction button in the present disclosure.

In the present embodiment, additional information is set to be added on a tomographic-image by tomographic-image basis. A plurality of kinds of additional information can be added to a single tomographic image. Specifically, user-added additional information added by a user and computer-added additional information added by a computer can be added as the plurality of kinds of additional information. Hereinafter, when the user-added additional information and the computer-added additional information are collectively referred to without being distinguished from each other, that is, when the user-added additional information and the computer-added additional information are collectively referred to without the kinds thereof being distinguished from each other, they are referred to as "additional information". When a tomographic image with the additional information is distinguished from a tomographic image without any additional information, the tomographic image with the additional information is referred to as a "specific tomographic image". In the present embodiment, the additional information is additional information unique to each specific tomographic image. The additional information added to each specific tomographic image and a marking (described later) corresponding to the additional information are associated with each other on a one-to-one basis. Examples of the user-added additional information include a bookmark added as a mark for a tomographic image which the user desires to observe later, and an annotation such as information on a region of interest (ROI) included in a tomographic image. Examples of the computer-added additional information include information on a region of interest detected through computer-aided diagnosis (CAD) or information on a region of interest detected through artificial intelligence (AI) image-based diagnosis. The region of interest used herein refers to a region to which the user pays attention, such as a region of a lesion such as a tumor. Examples of the information on a region of interest include an outline, a position, and an area of the region of interest. The computer that adds the computer-added additional information is not limited particularly. For example, one or more computers may add the computer-added additional information. For example, the computer that adds the computer-added additional information may be the display control apparatus 12, a control device included in the imaging apparatus 14, or the image storage apparatus 16. For example, the computer that adds the computer-added additional information may be a computer such as an image processing apparatus external to the diagnosis assistance system 10.

Figure 5:
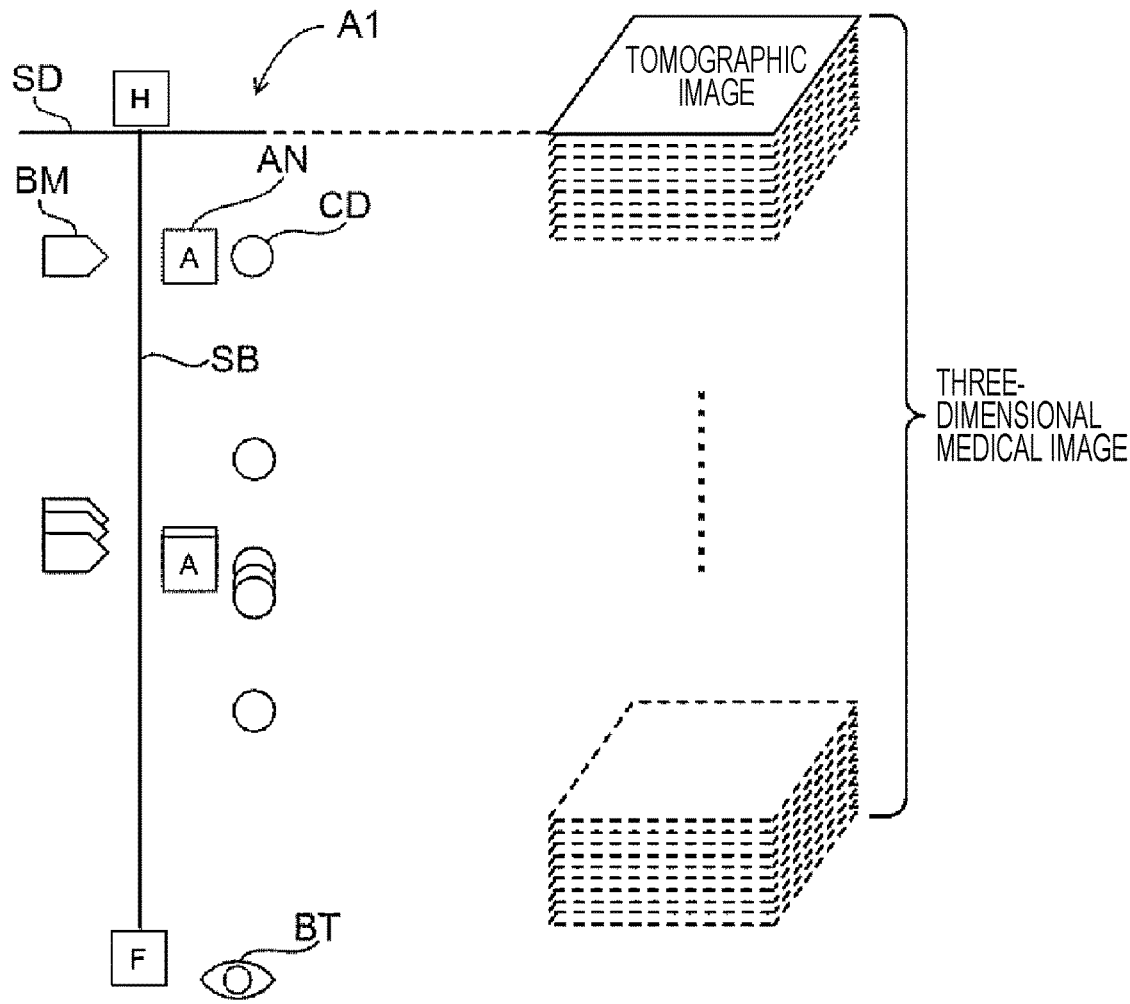
FIG. 5 is a diagram for describing the slider bar.

FIG. 5 illustrates only the display region A1 among the display regions A1, A2, and A3 illustrated in FIG. 4. The display control unit 42 performs control to display the slider SD at a position corresponding to the designated tomographic position in a longitudinal direction of the slider bar SB. In FIG. 5, "H" surrounded by a rectangle represents a head side of the subject, and "F" surrounded by a rectangle represents a foot side. That is, the position of the slider SD on the slider bar SB indicates a tomographic position closer to the head side as the position of the slider SD approaches "H" and indicates a tomographic position closer to the foot side as the position of the slider SD approaches "F" among the tomographic positions of the respective tomographic images constituting the three-dimensional medical image. FIG. 5 illustrates an example in which a tomographic position closest to the head side is designated from among the tomographic positions of the respective tomographic images constituting the three-dimensional medical image.

The display control unit 42 performs control to display, for a specific tomographic image with the additional information, a single marking that represents the additional information and with which a single tomographic image can be identified, at a position corresponding to the tomographic position of the tomographic image with the additional information on the slider bar SB.

Specifically, the display control unit 42 performs control to display, for a tomographic image with a bookmark, a marking BM representing the bookmark at a position corresponding to the tomographic position of the tomographic image with the bookmark on the slider bar SB. The display control unit 42 also performs control to display, for a tomographic image with an annotation, a marking AN representing the annotation at a position corresponding to the tomographic position of the tomographic image with the annotation on the slider bar SB. The display control unit 42 also performs control to display, for a specific tomographic image with computer-added additional information, a marking CD representing the computer-added additional information at a position corresponding to the tomographic position of the tomographic image with the computer-added additional information on the slider bar SB.

The display control unit 42 performs control to display the markings at respective positions corresponding to the tomographic position on the slider bar SB such that the markings are shifted from each other in a direction orthogonal to a longitudinal direction of the slider bar SB (that is, in a longitudinal direction of the slider SD). Thus, even if a plurality of markings are present for the same tomographic position, the markings do not overlap.

The display control unit 42 also performs control to display a button BT for receiving a user input for switching between displaying and hiding of the computer-added additional information.

Via the input unit 24, the user designates a tomographic position of a tomographic image desired to be displayed. For example, the user drags the slider SD to the tomographic position, on the slider bar SB, of the tomographic image desired to be displayed to designate the tomographic position. For example, the user scrolls a mouse wheel to designate the tomographic position, on the slider bar SB, of the tomographic image desired to be displayed.

Figure 6:
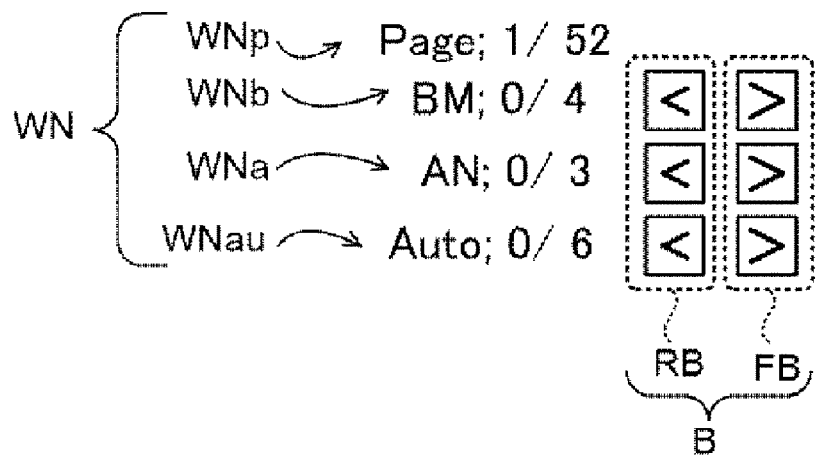
FIG. 6 is a diagram for describing the display information and the scroll buttons.

On the other hand, FIG. 6 illustrates only the display region A2 among the display regions A1, A2, and A3 illustrated in FIG. 4. In the display region A2, the display information WN and the plurality of scroll buttons B are displayed. The display control unit 42 performs control to display the display information WN and each of the plurality of scroll buttons B.

The display information WN is information indicating what number the tomographic image displayed in the display region A1 is. In the example illustrated in FIG. 6, a case where the tomographic image displayed in the display region A1 is an n-th tomographic image among m target tomographic images in total is represented by "n/m". Note that in the present embodiment, in one example, the position closest to the head side of the subject is set as the first, and the number indicating the order increases toward the foot side. Hereinafter, the number indicating the order in the display information WN is referred to as "order information".

In one example, the display information WN in the present embodiment includes display information WNp for display-target tomographic images, display information WNb for specific tomographic images with the bookmark, display information WNa for specific tomographic images with the annotation, and display information WNau for specific tomographic images with the computer-added additional information. The display information WNp is information indicating what number the displayed tomographic image is with respect to the total number of tomographic images set as the display target. FIG. 6 illustrates the display information WNp in the case where the total number of tomographic images set as the display targets is "52" and the "first" tomographic image is displayed. FIG. 6 also illustrates the display information WNb in the case where the total number of specific tomographic images with the bookmark is "4" and the displayed tomographic image is without any bookmark. FIG. 6 also illustrates the display information WNa in the case where the total number of specific tomographic images with the annotation is "3" and the displayed tomographic image is without any annotation. FIG. 6 also illustrates the display information WNau in the case where the total number of specific tomographic images with the computer-added additional information is "6" and the displayed tomographic image is without any computer-added additional information.

On the other hand, the scroll buttons B include forward buttons FB with which the user gives an instruction to forward the displayed tomographic image, and reverse buttons RB with which the user gives an instruction to reverse the displayed tomographic image. Note that in the present embodiment, the case of switching the displayed tomographic image in an order from a position closest to the head side of the subject toward a position closest to the foot side of the subject is referred to as "to forward". Conversely, in the present embodiment, the case of switching the displayed tomographic image in an order from the position closest to the foot side of the subject toward the position closest to the head side of the subject is referred to as "to reverse". Specifically, in response to the user clicking any of the scroll buttons B, an instruction to forward or reverse the displayed tomographic image is given. In response to any of the scroll buttons B being clicked, the reception unit 40 receives a specific display instruction. Note that a direction along the slider bar SB in the present embodiment is an example of a depth direction in the present disclosure. The forward order that is the order from the position closest to the head side of the subject toward the position closest to the foot side of the subject in the present embodiment is an example of a first order corresponding to a forward direction in the present disclosure. The reverse order that is the order from the position closest to the foot side of the subject toward the position closest to the head side of the subject in the present embodiment is an example of a second order corresponding to a reverse direction in the present disclosure.

In the present embodiment, a configuration will be described in which the user clicks any of the scroll buttons B to give an instruction to forward or reverse the displayed tomographic image. However, the way in which the user gives an instruction to forward or reverse is not limited to this configuration. For example, the user may operate a cursor-control key of a keyboard to give an instruction to forward or reverse. In a specific example of this case, the user may operate an up or right arrow cursor-control key to give an instruction to forward and may operate a down or left arrow cursor-control key to give an instruction to reverse.

In the present embodiment, as illustrated in FIG. 6, each of the forward button FB and the reverse button RB is provided for each of the display information WNb, the display information WNa, and the display information WNau. That is, in the present embodiment, a pair of the forward button FB and the reverse button RB is provided for tomographic images with the bookmark, for tomographic images with the annotation, and for specific tomographic images with the computer-added additional information.

Figure 7:
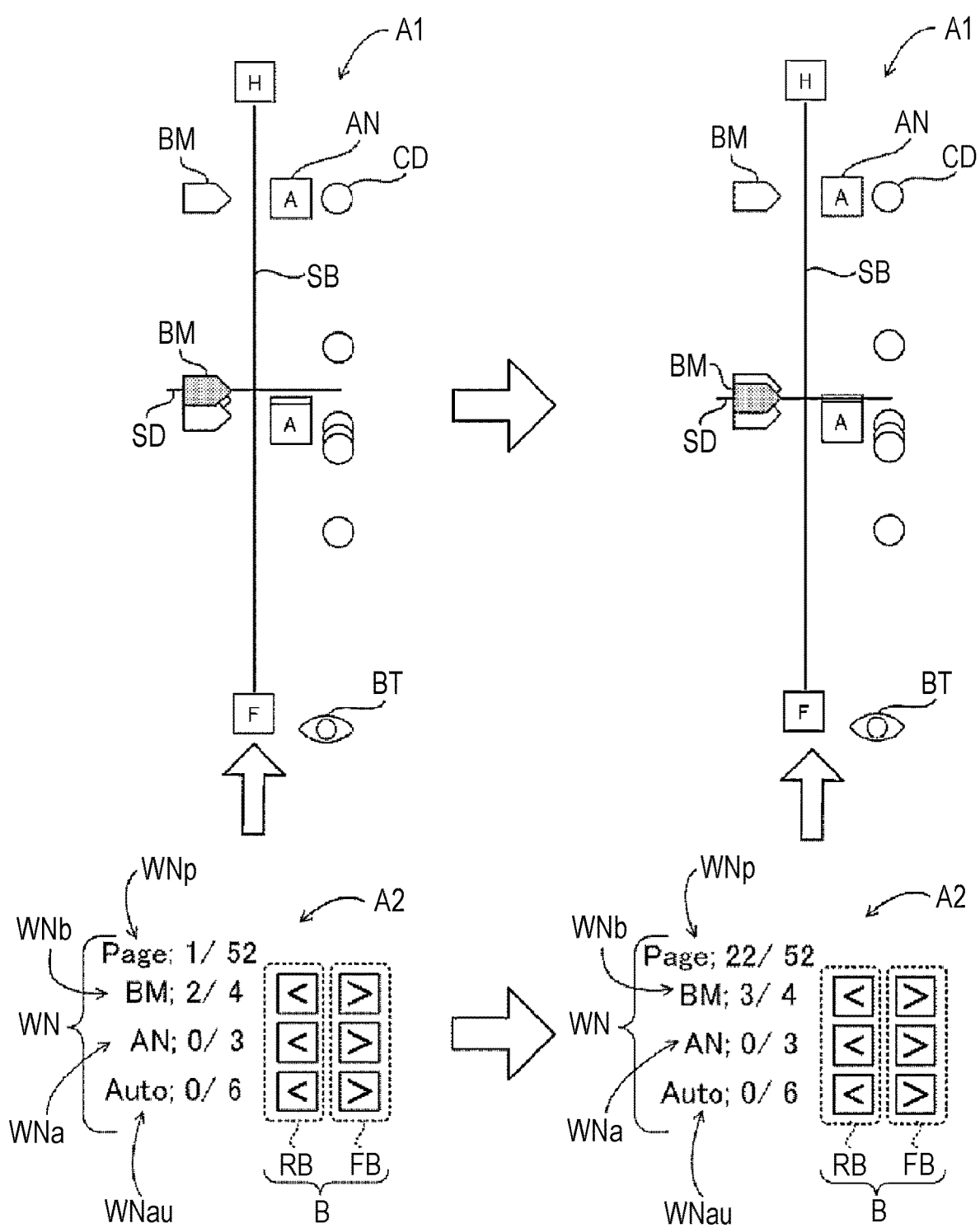
FIG. 7 is a diagram for describing an example of updating of order information.

FIG. 7 illustrates a display example in the case where the user clicks the forward button FB corresponding to the display information WNb when the second specific tomographic image, among the specific tomographic images with the bookmark, is displayed in the display region A3. In response to the user clicking the forward button FB corresponding to the display information WNb, the reception unit 40 receives an instruction to forward the specific tomographic image with the bookmark. In accordance with the instruction received by the reception unit 40, the display control unit 42 performs control to display, in the display region A3, the next specific tomographic image of the displayed specific tomographic image among the specific tomographic images with the bookmark, for example, the third specific tomographic image among the specific tomographic images with the bookmark in FIG. 7 (not illustrated). As illustrated in FIG. 7, the display control unit 42 performs control to increment the order information in the display information WNb. That is, the display control unit 42 changes the number indicating the order of the specific tomographic image in the display information WNb to a value incremented by 1. As illustrated in FIG. 7, the display control unit 42 according to the present embodiment performs control to display the slider SD at a position corresponding to the tomographic position of the displayed specific tomographic image in the longitudinal direction of the slider bar SB.

As described above, in response to the user clicking the scroll button B, that is, in response to the reception unit 40 receiving the specific display instruction, the display control unit 42 according to the present embodiment performs control to display, for each kind of the added additional information, only the specific tomographic images with the additional information in the forward or reverse order. In the present embodiment, in response to the user clicking the forward button FB or the reverse button RB corresponding to the display information WNb, the display control unit 42 performs control to display, in the display region A3, only the specific tomographic images with the bookmark in the forward or reverse order. In this case, even if a specific tomographic image with the additional information of another kind or a tomographic image without any additional information is present between an n-th specific tomographic image with the bookmark and an (n+1)-th specific tomographic image with the bookmark, such a tomographic image is not displayed in the display region A3. Likewise, in response to the user clicking the forward button FB or the reverse button RB corresponding to the display information WNa, the display control unit 42 performs control to display, in the display region A3, only the specific tomographic images with the annotation in the forward or reverse order. In this case, even if a specific tomographic image with the additional information of another kind or a tomographic image without any additional information is present between an n-th specific tomographic image with the annotation and an (n+1)-th specific tomographic image with the annotation, such a tomographic image is not displayed in the display region A3. In response to the user clicking the forward button FB or the reverse button RB corresponding to the display information WNau, the display control unit 42 performs control to display, in the display region A3, only the specific tomographic images with the computer-added additional information in the forward or reverse order. In this case, even if a specific tomographic image with the additional information of another kind or a tomographic image without any additional information is present between an n-th specific tomographic image with the computer-added additional information and an (n+1)-th specific tomographic image with the computer-added additional information, such a tomographic image is not displayed in the display region A3.

As described above, in response to the user clicking the forward button FB corresponding to the display information WNb for the specific tomographic images with the bookmark, the display control unit 42 performs control to increment the order information of the display information WNb. On the other hand, in response to the user clicking the reverse button RB corresponding to the display information WNb for the specific tomographic images with the bookmark, the display control unit 42 performs control to decrement the order information of the display information WNb. In response to the user clicking the forward button FB corresponding to the display information WNa for the specific tomographic images with the annotation, the display control unit 42 performs control to increment the order information of the display information WNa. In response to the user clicking the reverse button RB corresponding to the display information WNa for the specific tomographic images with the annotation, the display control unit 42 performs control to decrement the order information of the display information WNa. In response to the user clicking the forward button FB corresponding to the display information WNau for the specific tomographic images with the computer-added additional information, the display control unit 42 performs control to increment the order information of the display information WNau. In response to the user clicking the reverse button RB corresponding to the display information WNau for the specific tomographic images with the computer-added additional information, the display control unit 42 performs control to decrement the order information of the display information WNau.

As illustrated in FIG. 7, if the tomographic image displayed in the display region A3 is a tomographic image with the additional information, the display control unit 42 according to the present embodiment performs control to display a marking provided at the position corresponding to the tomographic position of the displayed specific tomographic image on the slider bar SB, in a color (for example, orange) different from a color (normal color) of the other markings. In the example illustrated in FIG. 7, in response to the user clicking the forward button FB corresponding to the display information WNb, the display control unit 42 performs control to return the color of the marking BM for the second tomographic image with the bookmark to the same color as the color (normal color) of the other markings and to change the color of the marking BM for the third tomographic image with the bookmark to the color (orange) different from the color of the other markings.

Displaying the marking provided at the position corresponding to the tomographic position of the displayed specific tomographic image on the slider bar SB, in the color different from the color of the other markings in the present embodiment is an example of emphasized display in the present disclosure. The method of emphasized display is not limited to that of the present embodiment. Any method for emphasizing the marking provided at the position corresponding to the tomographic position of the displayed specific tomographic image on the slider bar SB may be used. For example, instead of making the color of the entire marking different as described above, emphasized display may be performed by making the color of the outline of the marking different. For example, emphasized display may be performed by displaying only the marking corresponding to the designated tomographic position to blink.

Figure 8:
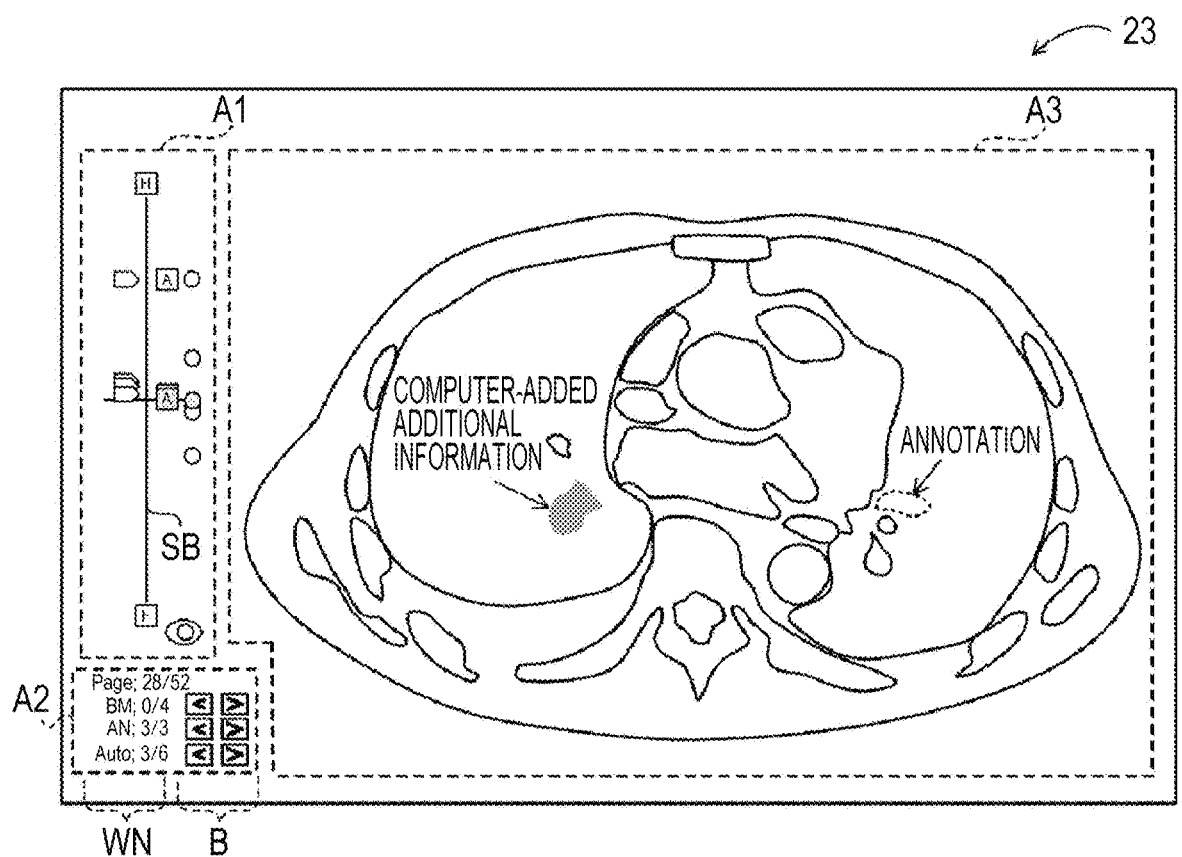
FIG. 8 is a diagram illustrating an example of computer-added additional information and an annotation which is one piece of user-added additional information displayed over a tomographic image.

As illustrated in FIG. 8, for a specific tomographic image with the computer-added additional information, the display control unit 42 performs control to display the computer-added additional information over the specific tomographic image. Specifically, for example, the display control unit 42 performs control to display a region of interest represented by the computer-added additional information in a state of being filled with a color (for example, orange) different from the color of the other region.

As illustrated in FIG. 8, for a tomographic image with the annotation, the display control unit 42 performs control to display the annotation over the tomographic image. Specifically, for example, the display control unit 42 performs control to display the outline of the region of interest represented by the annotation in a color (for example, white) different from the color of the region of interest represented by the computer-added additional information. Thus, the user can grasp whether the region of interest displayed in the tomographic image is detected through a user operation or by a computer. In FIG. 8, for ease of understanding, the outline of the region of interest represented by the annotation, which is a white solid outline, is illustrated as a broken line.

In detection by a computer, many regions of interest may be detected. Accordingly, before performing image-based diagnosis, the user may desire to hide the computer-added additional information. When the user desires to switch between displaying and hiding of the computer-added additional information, the user designates the button BT via the input unit 24.

Figure 9:
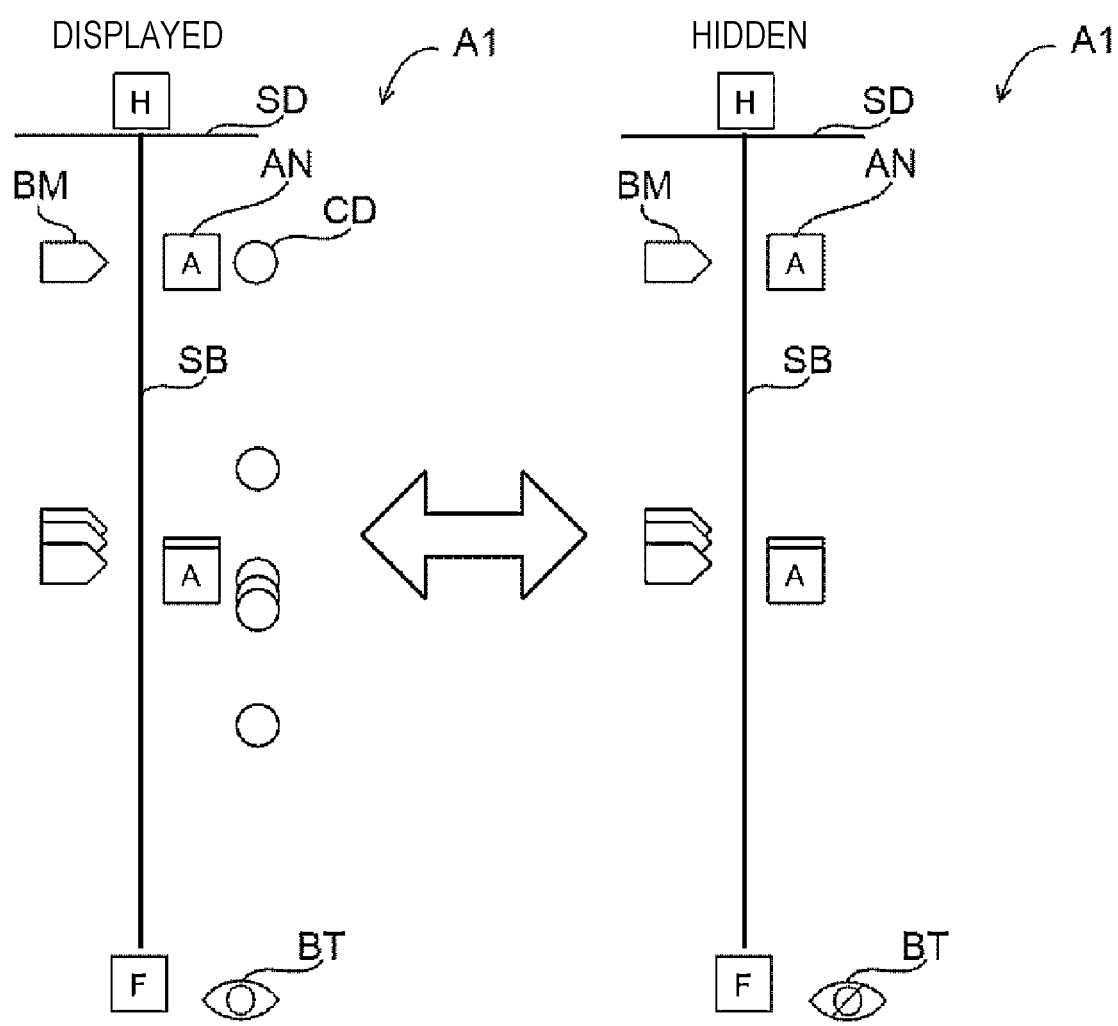
FIG. 9 is a diagram for describing switching between displaying and hiding of a marking representing the computer-added additional information.
Figure 10:
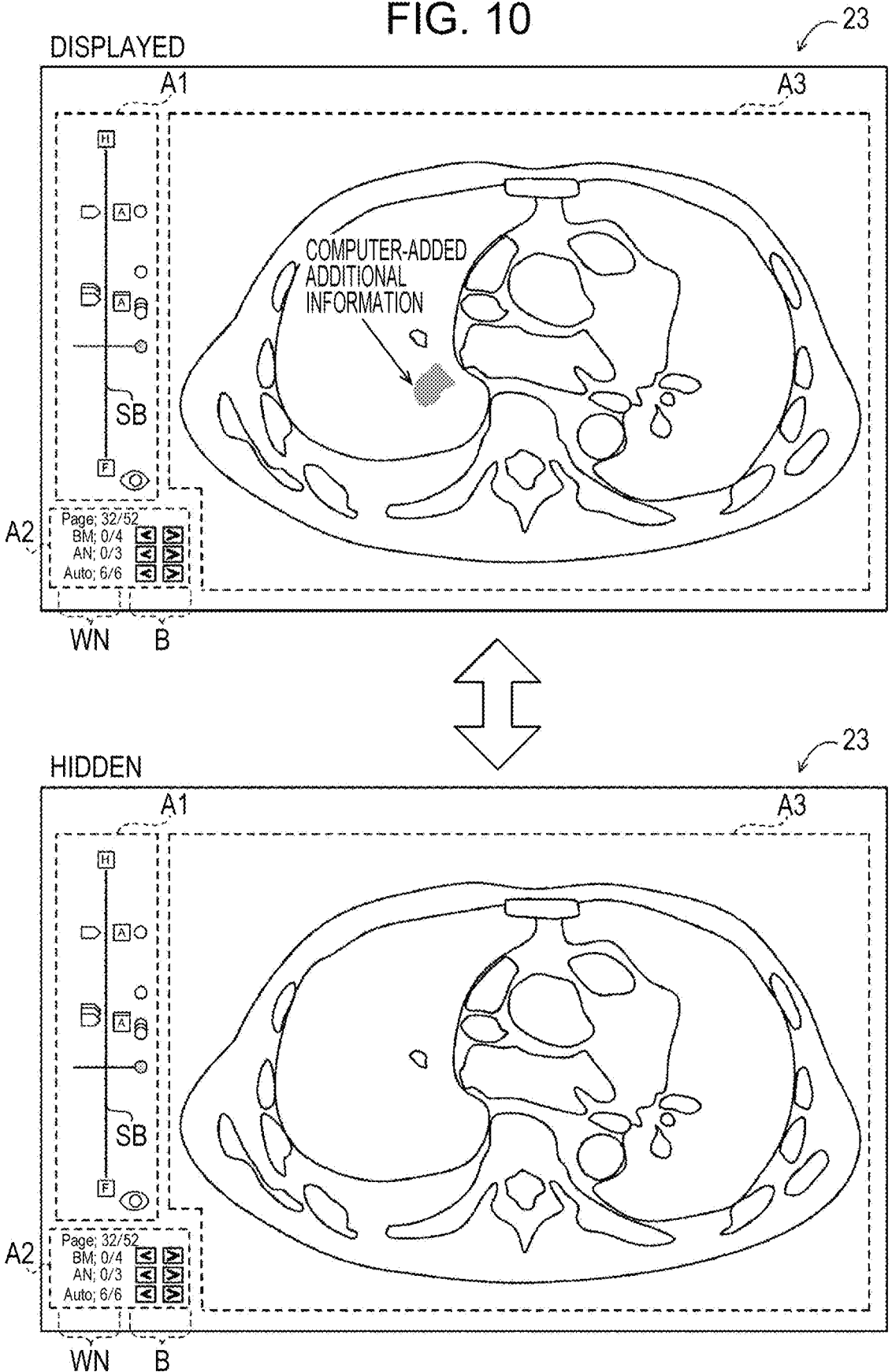
FIG. 10 is a diagram for describing switching between displaying and hiding of the computer-added additional information over a tomographic image.

In response to the reception unit 40 receiving an input for switching between displaying and hiding of the computer-added additional information, the display control unit 42 performs control to switch between displaying and hiding of the marking CD representing the computer-added additional information in accordance with the received input, as illustrated in FIG. 9. In the present embodiment, the display control unit 42 also performs control to switch between displaying and hiding of the computer-added additional information over the tomographic image in addition to the marking CD, as illustrated in FIG. 10.

Figure 11:
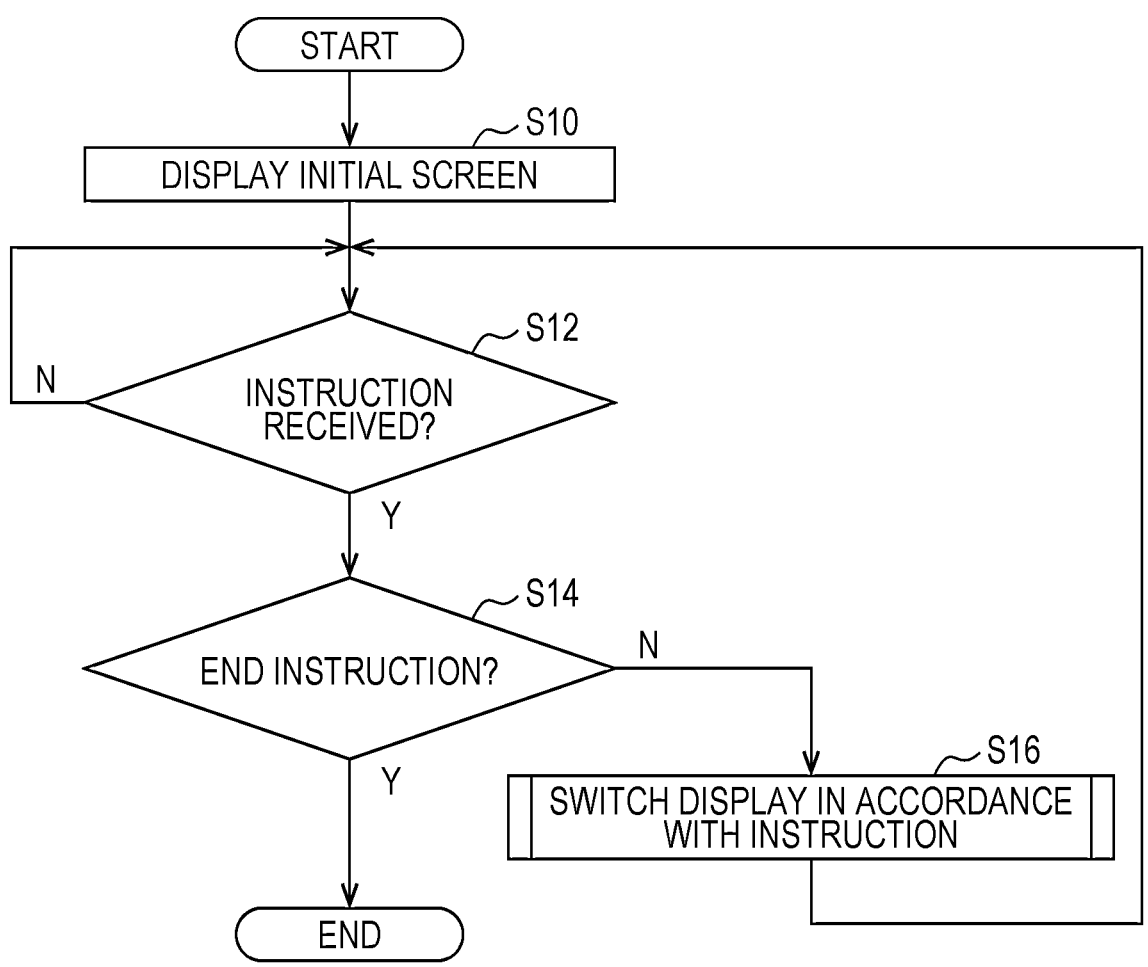
FIG. 11 is a flowchart illustrating an example of a display control process.

An operation of the display control apparatus 12 according to the present embodiment will be described next with reference to FIG. 11. The CPU 20 executes the display control program 30, so that a display control process illustrated in FIG. 11 is performed. The display control process is performed, for example, in response to the user inputting, via the input unit 24, an execution instruction and identification information with which a group of tomographic images constituting a display-target three-dimensional medical image is identifiable.

In step S10 in FIG. 11, the display control unit 42 acquires the group of tomographic images identified in accordance with the input identification information from the image storage apparatus 16, and performs control to display an initial screen on the display 23 based on the acquired group of tomographic images. Specifically, as described above, the display control unit 42 performs control to display, on the display 23, the slider bar SB for designating a tomographic position corresponding to each of the acquired tomographic images in the group, the tomographic image corresponding to the designated tomographic position, the display information WN, and the scroll buttons B. As described above, the display control unit 42 also performs control to display the slider SD at the position corresponding to the designated tomographic position in the longitudinal direction of the slider bar SB. An example will be described in which the tomographic position closest to the head side is used as the designated tomographic position in the initial screen. However, the designated tomographic position is not limited to this. In the initial screen, the tomographic position closest to the foot side or the tomographic position at the center may be used as the designated tomographic position.

As described above, the display control unit 42 performs control to display, for a specific tomographic image with the additional information among the tomographic images in the group, the marking representing the additional information at the position corresponding to the tomographic position of the tomographic image with the additional information on the slider bar SB. The display control unit 42 also performs control to display the button BT for receiving a user input for switching between displaying and hiding of the computer-added additional information. As a result of the processing of step S10, the screen illustrated in FIG. 4 is displayed on the display 23, for example. Note that when step S10 is performed for the second and subsequent times, the display control unit 42 sets the display state in which the most recent display state is inherited.

In step S12, the reception unit 40 waits until the reception unit 40 receives an instruction input by the user via the input unit 24. In response to the instruction being input by the user via the input unit 24, the determination in step S12 is positive and thus the process proceeds to step S14. In step S14, the reception unit 40 determines whether or not the instruction received in step S12 is an instruction to end the display. If this determination is negative, the process proceeds to step S16. In step S16, the display control unit 42 performs control to switch the display in accordance with the instruction received in step S12. In response to the end of the processing of step S16, the process returns to step S12. On the other hand, if the determination in step S14 is positive, the display control process ends. The display state of the display objects displayed in the respective display regions A1, A2, and A3 at the time when this display control process ends is stored in the image storage apparatus 16 in association with the group of tomographic images, for example, so that the display state is inherited when step S10 is performed for the second and subsequent times.

Figure 12:
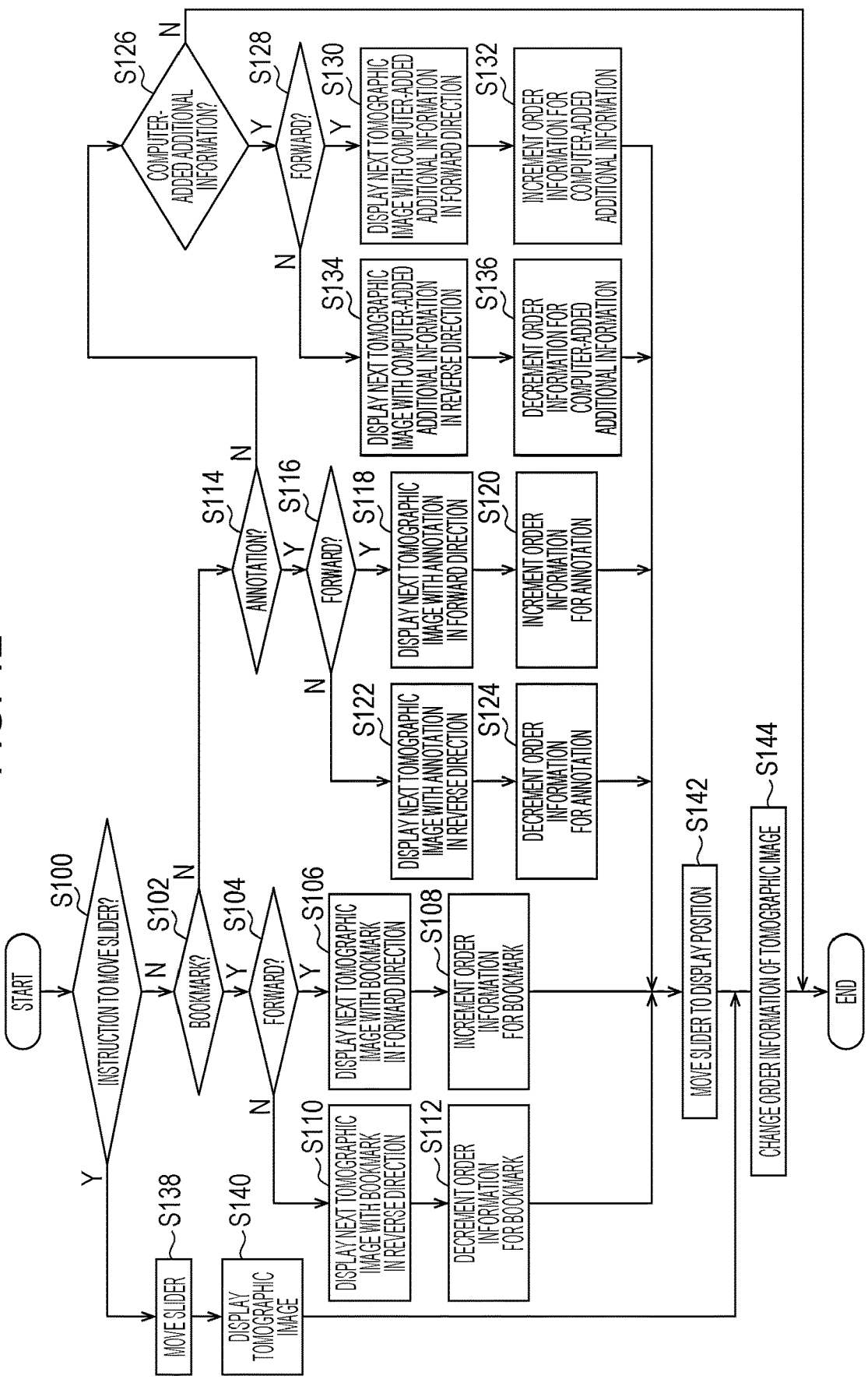
FIG. 12 is a flowchart illustrating an example of a processing routine in S16 of the display control process.

If the instruction received in step S12 is an instruction to designate a tomographic position through a drag operation on the slider SD, a scroll operation on a mouse wheel, or the like, or is an instruction to forward or reverse the tomographic image via the scroll button B, a processing routine illustrated in FIG. 12 is performed in step S16.

In step S100 in FIG. 12, the display control unit 42 determines whether or not the instruction received in step S12 above is an instruction to move the slider SD through a drag operation on the slider SD, a scroll operation on the mouse wheel, or the like. If the instruction received in step S12 is not an instruction to move the slider SD, the determination in step S100 is negative. For example, if the instruction received in step S12 above results from clicking of the scroll button B, that is, if the received instruction is the specific display instruction, the determination in step S100 is negative and thus the process proceeds to step S102.

In step S102, the display control unit 42 determines whether or not the instruction received in step S12 above is the specific display instruction received as a result of clicking of the forward button FB or the reverse button RB corresponding to the display information WNb for the specific tomographic images with the bookmark. If the specific display instruction resulting from clicking of the forward button FB or the reverse button RB corresponding to the display information WNb is received, the determination in step S102 is positive and thus the process proceeds to step S104.

In step S104, the display control unit 42 determines whether or not the instruction received in step S12 above is the specific display instruction received as a result of clicking of the forward button FB. If the specific display instruction resulting from clicking of the forward button FB is received, the determination in step S104 is positive and thus the process proceeds to step S106.

In step S106, the display control unit 42 performs control to display, in the display region A3, the next specific tomographic image with the bookmark in the forward direction. Specifically, in the case of a state in which an n-th specific tomographic image among the specific tomographic images with the bookmark is displayed in the display region A3, the display control unit 42 performs control to display an (n+1)-th specific tomographic image in the display region A3. If the user clicks the forward button FB corresponding to the display information WNb in a state in which a tomographic image without any bookmark is displayed in the display region A3, the display control unit 42 performs control to display, in the display region A3, the specific tomographic image with the bookmark that is at the tomographic position closest to the tomographic position of the tomographic image currently in the display region A3 in the forward direction. The display control unit 42 also performs control to move the slider SD to the position, on the slider bar SB, corresponding to the tomographic position of the specific tomographic image displayed in the display region A3.

If the user clicks the forward button FB corresponding to the display information WNb in a state in which the tomographic image at the tomographic position closest to the foot side of the subject is displayed in the display region A3, there is no tomographic image of which the tomographic position is in the forward direction relative to the tomographic image currently displayed in the display region A3. In this case, the display control unit 42 may perform control to keep displaying the tomographic image currently displayed in the display region A3 as it is. In this case, the display control unit 42 may skip this step. In such a case, the display control unit 42 preferably performs control to display, on the display 23, information indicating that there is no specific tomographic image to be displayed.

In next step S108, the display control unit 42 increments the order information of the display information WNb. In response to the end of the processing of step S108, the process proceeds to step S142.

On the other hand, if the specific display instruction resulting from clicking of the forward button FB is not received in step S104 above, that is, if the specific display instruction resulting from clicking of the reverse button RB is received, the determination is negative and thus the process proceeds to step S110.

In step S110, the display control unit 42 performs control to display, in the display region A3, the next specific tomographic image with the bookmark in the reverse direction. Specifically, in the case of a state in which an n-th specific tomographic image among the specific tomographic images with the bookmark is displayed in the display region A3, the display control unit 42 performs control to display an (n−1)-th specific tomographic image in the display region A3. If the user clicks the reverse button RB corresponding to the display information WNb in a state in which a tomographic image without any bookmark is displayed in the display region A3, the display control unit 42 performs control to display, in the display region A3, the specific tomographic image with the bookmark that is at the tomographic position closest to the tomographic position of the tomographic image currently displayed in the display region A3 in the reverse direction. The display control unit 42 also performs control to move the slider SD to the position, on the slider bar SB, corresponding to the tomographic position of the specific tomographic image displayed in the display region A3.

If the user clicks the reverse button RB corresponding to the display information WNb in a state in which the tomographic image at the tomographic position closest to the head side of the subject is displayed in the display region A3, there is no tomographic image of which the tomographic position is in the reverse direction relative to the tomographic image currently displayed in the display region A3. In this case, the display control unit 42 may perform control to keep displaying the tomographic image currently displayed in the display region A3 as it is. In this case, the display control unit 42 may skip this step. In such a case, the display control unit 42 preferably performs control to display, on the display 23, information indicating that there is no specific tomographic image to be displayed.

In next step S112, the display control unit 42 decrements the order information of the display information WNb. In response to the end of the processing of step S112, the process proceeds to step S142.

On the other hand, if the instruction received in step S12 above is not the specific display instruction resulting from clicking of the forward button FB or the reverse button RB corresponding to the display information WNb for the specific tomographic images with the bookmark in step S102 above, the determination in step S102 is negative and thus the process proceeds to step S114.

In step S114, the display control unit 42 determines whether or not the instruction received in step S12 above is the specific display instruction received as a result of clicking of the forward button FB or the reverse button RB corresponding to the display information WNa for the specific tomographic image with the annotation. If the specific display instruction resulting from clicking of the forward button FB or the reverse button RB corresponding to the display information WNa is received, the determination in step S114 is positive and thus the process proceeds to step S116.

In step S116, the display control unit 42 determines whether or not the instruction received in step S12 above is the specific display instruction received as a result of clicking of the forward button FB. If the specific display instruction resulting from clicking of the forward button FB is received, the determination in step S116 is positive and thus the process proceeds to step S118.

In step S118, the display control unit 42 performs control to display, in the display region A3, the next specific tomographic image with the annotation in the forward direction. Specifically, in the case of a state in which an n-th specific tomographic image among the specific tomographic images with the annotation is displayed in the display region A3, the display control unit 42 performs control to display an (n+1)-th specific tomographic image in the display region A3. If the user clicks the forward button FB corresponding to the display information WNa in a state in which a tomographic image without any annotation is displayed in the display region A3, the display control unit 42 performs control to display, in the display region A3, the specific tomographic image with the annotation that is at the tomographic position closest to the tomographic position of the tomographic image currently in the display region A3 in the forward direction. The display control unit 42 also performs control to move the slider SD to the position, on the slider bar SB, corresponding to the tomographic position of the specific tomographic image displayed in the display region A3.

If the user clicks the forward button FB corresponding to the display information WNa in a state in which the tomographic image at the tomographic position closest to the foot side of the subject is displayed in the display region A3, there is no tomographic image of which the tomographic position is in the forward direction relative to the tomographic image currently in the display region A3. In this case, the display control unit 42 may perform control to keep displaying the tomographic image currently displayed in the display region A3 as it is. In this case, the display control unit 42 may skip this step. In such a case, the display control unit 42 preferably performs control to display, on the display 23, information indicating that there is no specific tomographic image to be displayed.

In next step S120, the display control unit 42 increments the order information of the display information WNa. In response to the end of the processing of step S120, the process proceeds to step S142.

On the other hand, if the specific display instruction resulting from clicking of the forward button FB is not received in step S116 above, that is, if the specific display instruction resulting from clicking of the reverse button RB is received, the determination is negative and thus the process proceeds to step S122.

In step S122, the display control unit 42 performs control to display, in the display region A3, the next specific tomographic image with the annotation in the reverse direction. Specifically, in the case of a state in which an n-th specific tomographic image among the specific tomographic images with the annotation is displayed in the display region A3, the display control unit 42 performs control to display an (n−1)-th specific tomographic image in the display region A3. In response to the user clicking the reverse button RB corresponding to the display information WNa in a state in which a tomographic image without any annotation is displayed in the display region A3, the display control unit 42 performs control to display, in the display region A3, the specific tomographic image with the annotation that is at the tomographic position closest to the tomographic position of the tomographic image currently in the display region A3 in the reverse direction. The display control unit 42 also performs control to move the slider SD to the position, on the slider bar SB, corresponding to the tomographic position of the specific tomographic image displayed in the display region A3.

If the user clicks the reverse button RB corresponding to the display information WNa in a state in which the tomographic image at the tomographic position closest to the head side of the subject is displayed in the display region A3, there is no tomographic image of which the tomographic position is in the reverse direction relative to the tomographic image currently in the display region A3. In this case, the display control unit 42 may perform control to keep displaying the tomographic image currently displayed in the display region A3 as it is. In this case, the display control unit 42 may skip this step. In such a case, the display control unit 42 preferably performs control to display, on the display 23, information indicating that there is no specific tomographic image to be displayed.

In next step S124, the display control unit 42 decrements the order information of the display information WNa. In response to the end of the processing of step S124, the process proceeds to step S142.

On the other hand, if the instruction received in step S12 above is not the specific display instruction as a result of clicking of the forward button FB or the reverse button RB corresponding to the display information WNa for the specific tomographic images with the annotation in step S114 above, the determination in step S114 is negative and thus the process proceeds to step S126.

In step S126, the display control unit 42 determines whether or not the instruction received in step S12 above is the specific display instruction received as a result of clicking of the forward button FB or the reverse button RB corresponding to the display information WNau for the specific tomographic images with the computer-added additional information. If the specific display instruction resulting from clicking of the forward button FB or the reverse button RB corresponding to the display information WNau is received, the determination in step S126 is positive and thus the process proceeds to step S128.

In step S128, the display control unit 42 determines whether or not the instruction received in step S12 above is the specific display instruction received as a result of clicking of the forward button FB. If the specific display instruction resulting from clicking of the forward button FB is received, the determination in step S128 is positive and thus the process proceeds to step S130.

In step S130, the display control unit 42 performs control to display, in the display region A3, the next specific tomographic image with the computer-added additional information in the forward direction. Specifically, in the case of a state in which an n-th specific tomographic image among the specific tomographic images with the computer-added additional information is displayed in the display region A3, the display control unit 42 performs control to display an (n+1)-th specific tomographic image in the display region A3. If the user clicks the forward button FB corresponding to the display information WNau in a state in which a tomographic image without any computer-added additional information is displayed in the display region A3, the display control unit 42 performs control to display, in the display region A3, the specific tomographic image with the computer-added additional information that is at the tomographic position closest to the tomographic position of the tomographic image currently in the display region A3 in the forward direction. The display control unit 42 also performs control to move the slider SD to the position, on the slider bar SB, corresponding to the tomographic position of the specific tomographic image displayed in the display region A3.

If the user clicks the forward button FB corresponding to the display information WNau in a state in which the tomographic image at the tomographic position closest to the foot side of the subject is displayed in the display region A3, there is no tomographic image of which the tomographic position is in the forward direction relative to the tomographic image currently in the display region A3. In this case, the display control unit 42 may perform control to keep displaying the current tomographic image in the display region A3 as it is. In this case, the display control unit 42 may skip this step. In such a case, the display control unit 42 preferably performs control to display, on the display 23, information indicating that there is no specific tomographic image to be displayed.

In next step S132, the display control unit 42 increments the order information of the display information WNau. In response to the end of the processing of step S132, the process proceeds to step S142.

On the other hand, if the specific display instruction resulting from clicking of the forward button FB is not received in step S128 above, that is, if the specific display instruction resulting from clicking of the reverse button RB is received, the determination is negative and thus the process proceeds to step S134.

In step S134, the display control unit 42 performs control to display, in the display region A3, the next specific tomographic image with the computer-added additional information in the reverse direction. Specifically, in the case of a state in which an n-th specific tomographic image among the specific tomographic images with the computer-added additional information is displayed in the display region A3, the display control unit 42 performs control to display an (n−1)-th specific tomographic image in the display region A3. If the user clicks the reverse button RB corresponding to the display information WNau in a state in which a tomographic image without any computer-added additional information is displayed in the display region A3, the display control unit 42 performs control to display, in the display region A3, the specific tomographic image with the computer-added additional information that is at the tomographic position closest to the tomographic position of the tomographic image currently in the display region A3 in the reverse direction. The display control unit 42 also performs control to move the slider SD to the position, on the slider bar SB, corresponding to the tomographic position of the specific tomographic image displayed in the display region A3.

If the user clicks the reverse button RB corresponding to the display information WNau in a state in which the tomographic image at the tomographic position closest to the head side of the subject is displayed in the display region A3, there is no tomographic image of which the tomographic position is in the reverse direction relative to the tomographic image currently in the display region A3. In this case, the display control unit 42 may perform control to keep displaying the current tomographic image in the display region A3 as it is. In this case, the display control unit 42 may skip this step. In such a case, the display control unit 42 preferably performs control to display, on the display 23, information indicating that there is no specific tomographic image to be displayed.

In next step S136, the display control unit 42 decrements the order information of the display information WNa. In response to the end of the processing of step S136, the process proceeds to step S142.

In step S142, the display control unit 42 performs control to move the slider SD to the position, on the slider bar SB, corresponding to the tomographic position of the tomographic image displayed in the display region A3 in the processing of any of steps S106, S110, S118, S122, S130, and S134 above.

On the other hand, if the received instruction is an instruction to move the slider SD resulting from a drag operation on the slider SD, a scroll operation on the mouse wheel, or the like in step S100 above, the determination is positive and thus the process proceeds to step S138.

In step S138, the display control unit 42 performs control to move the slider SD to the position, on the slider bar SB, corresponding to the tomographic position designated through the user operation. In next step S140, the display control unit 42 performs control to switch the tomographic image in the display region A3 to the tomographic image at the designated tomographic position. In response to the end of the processing of step S140, the process proceeds to step S144.

In step S144, the display control unit 42 changes the order information of the display information WNp to a value corresponding to the order of the tomographic image displayed in the display region A3 in the processing of any of steps S106, S110, S118, S122, S130, S134, and S140.

In response to the end of the processing of step S144, the processing routine illustrated in FIG. 12 ends. If the determination in step S126 above is negative, the processing routine illustrated in FIG. 12 also ends.

Figure 13:
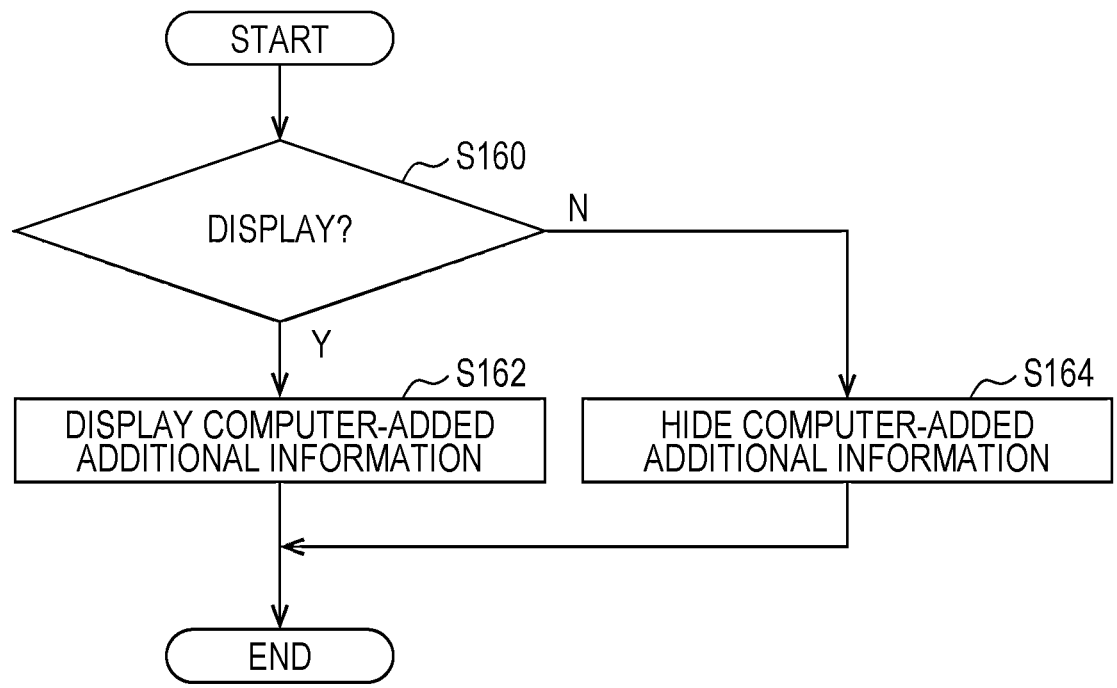
FIG. 13 is a flowchart illustrating an example of a processing routine for switching between displaying and hiding of the computer-added additional information.

If the instruction received in step S12 is an instruction to switch between displaying and hiding of the computer-added additional information as a result of designation of the button BT, a processing routine illustrated in FIG. 13 is performed in step S16.

In step S160 in FIG. 13, the reception unit 40 determines whether or not the received instruction is an instruction to display the computer-added additional information. If this determination is positive, the process proceeds to step S162. If the instruction received by the reception unit 40 is an instruction to hide the computer-added additional information, the determination in step S160 is negative and thus the process proceeds to step S164.

In step S162, the display control unit 42 performs control to display the marking CD representing the computer-added additional information and to display the computer-added additional information over the tomographic image as described above. In response to the end of the processing of step S162, the processing routine illustrated in FIG. 13 ends.

In step S164, the display control unit 42 performs control to hide the marking CD representing the computer-added additional information and to hide the computer-added additional information over the tomographic image as described above. In response to the end of the processing of step S164, the processing routine illustrated in FIG. 13 ends.

As described above, the display control apparatus 12 according to the present embodiment is the display control apparatus 12 including the CPU 20 as at least one processor. The CPU 20 displays the slider bar SB and the slider SD for designating a tomographic position corresponding to each of a plurality of tomographic images for medical use obtained through imaging of a subject. The CPU 20 also displays a tomographic image corresponding to the tomographic position designated by the slider SD. For each of one or more specific tomographic images with additional information, which is set to be added on a tomographic-image by tomographic-image basis, the CPU 20 also displays a marking representing the additional information at a position corresponding to a tomographic position of the tomographic image in a depth direction of the slider bar SB. The CPU 20 receives a specific display instruction to display, among the plurality of tomographic images, only the specific tomographic images that are on either side of the slider bar SB in the depth direction with respect to a reference that is a current position designated by the slider SD. In response to receiving the specific display instruction, the CPU 20 displays only the specific tomographic images in an order according to the depth direction. In response to only the specific tomographic images being displayed in the order according to the depth direction, the CPU 20 displays the marking representing the additional information added to the respective specific tomographic images in an emphasized manner in the order according to the depth direction.

As described above, according to the present embodiment, in response to the instruction from the user, control is performed to display only the specific tomographic images with the additional information in the order according to the depth direction of the plurality of tomographic images. Thus, for example, even if the user does not perform an operation such as dragging the slider SD to a position of a specific tomographic image with a marking indicating that the additional information is added on the slider bar SB, only the specific tomographic images with the additional information can be displayed in the order according to the depth direction. The display control apparatus 12 according to the present embodiment allows the user to consecutively observe only the specific tomographic images with the additional information while skipping the tomographic images that are without any additional information and thus are less likely to be observed by the user than the specific tomographic images with the additional information.

Thus, the display control apparatus 12 according to the present embodiment can make it easier to observe the specific tomographic image with the additional information.

Note that the display manner and the display method of the display information WN and the scroll buttons B are not limited to the manner and the method described above. For example, first and second modifications below may be employed.

First Modification

In the above, the configuration has been described in which the display information WN and the scroll buttons B are displayed adjacently in combination for each kind of the additional information. Specifically, the configuration has been described in which the display control unit 42 simultaneously displays three kinds of display information WN for the bookmark WNb, the annotation WNa, and the computer-added additional information WNau, and the scroll buttons B corresponding to the respective kinds of display information WN in the display region A2. By contrast, in the present modification, a configuration will be described in which the display control unit 42 performs control to display, in the display region A2, only the display information WN and the scroll buttons B corresponding to the additional information of the kind selected by the user from among the plurality of kinds of additional information.

Figure 14:
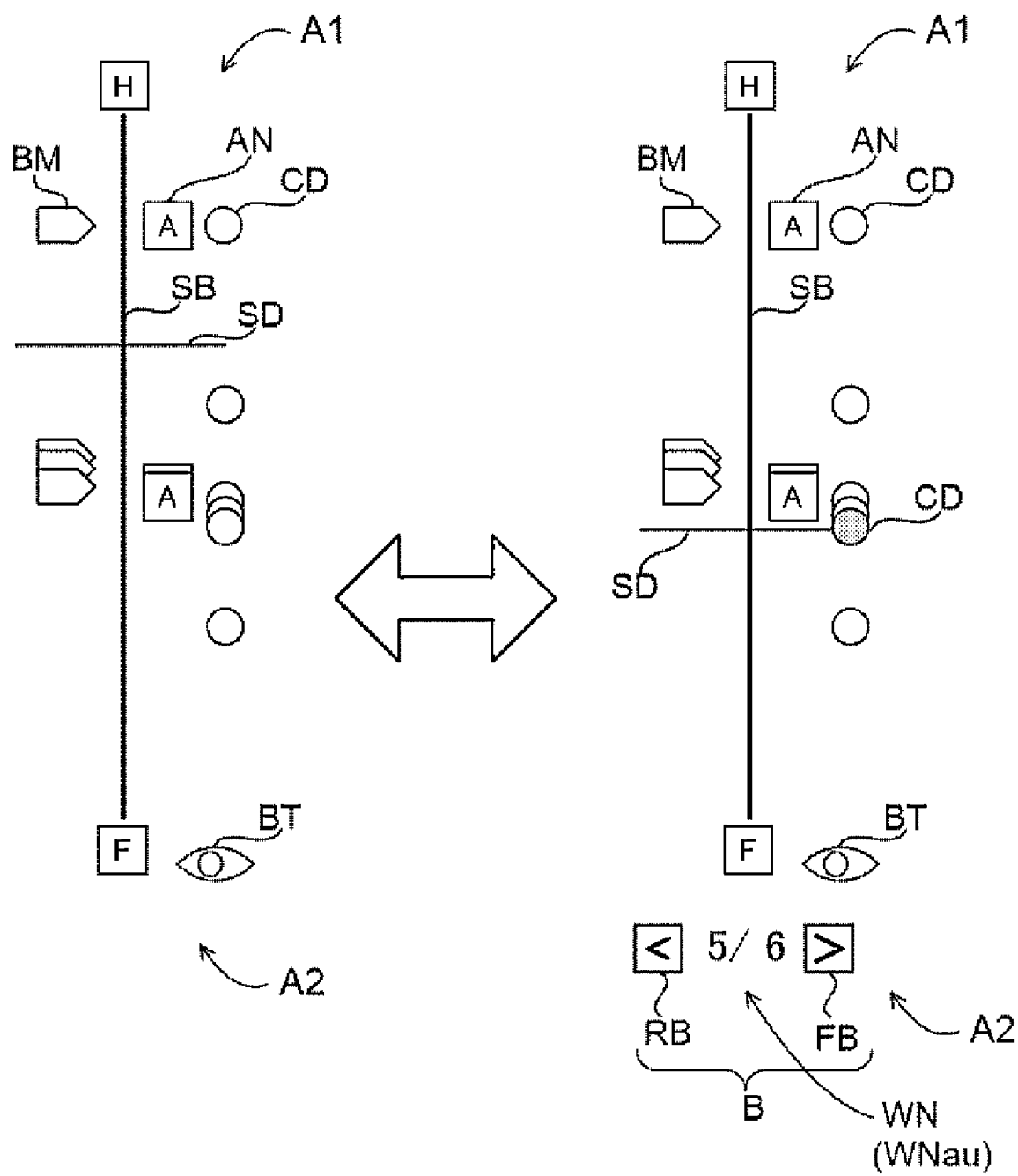
FIG. 14 is a diagram for describing display information and scroll buttons according to a first modification.

In one example, in the present modification, as illustrated in FIG. 14, when there is no marking corresponding to the additional information at the position of the slider SD on the slider bar SB, that is, when no additional information is added to the tomographic image displayed in the display region A3, the display control unit 42 performs control to hide the display information WN and the scroll buttons B. That is, as illustrated in FIG. 14, nothing is displayed in the display region A2. In the present modification, if the user drags the slider SD, the display control unit 42 performs control to hide the display information WN and the scroll buttons B in the display region A2 as illustrated in a left-side diagram of FIG. 14.

On the other hand, if the user designates, through clicking, the marking corresponding to the additional information at the position of the slider bar SB, the display control unit 42 performs control to display, in the display region A2, the display information WN and the scroll buttons B corresponding to the additional information of the kind indicated by the designated marking. That is, the user can cause the display information WN and the scroll buttons B to be displayed in the display region A2 for the desired kind of additional information by designating the marking corresponding to the additional information at the position of the slider bar SB.

In one example, a right-side diagram of FIG. 14 illustrates a state in which the marking CD representing the computer-added additional information is clicked by the user. In this case, as illustrated in FIG. 14, the display control unit 42 performs control to display, in the display region A2, the display information WNau as the display information WN and the scroll buttons B. As described above, if the user drags the slider SD in this state, the display control unit 42 performs control to hide the display information WN and the scroll buttons B in the display region A2, which results in a state in which nothing is displayed in the display region A2 as illustrated in the left-side diagram of FIG. 14.

An operation of the display control apparatus 12 according to the present modification will be described next with reference to FIG. 15.

In the display control process (see FIG. 11) of the present modification, a processing routine performed in step S16 is different from the processing routine described with reference to FIG. 12 above. FIG. 15 illustrates an example of the processing routine performed in the present modification.

Figure 15:
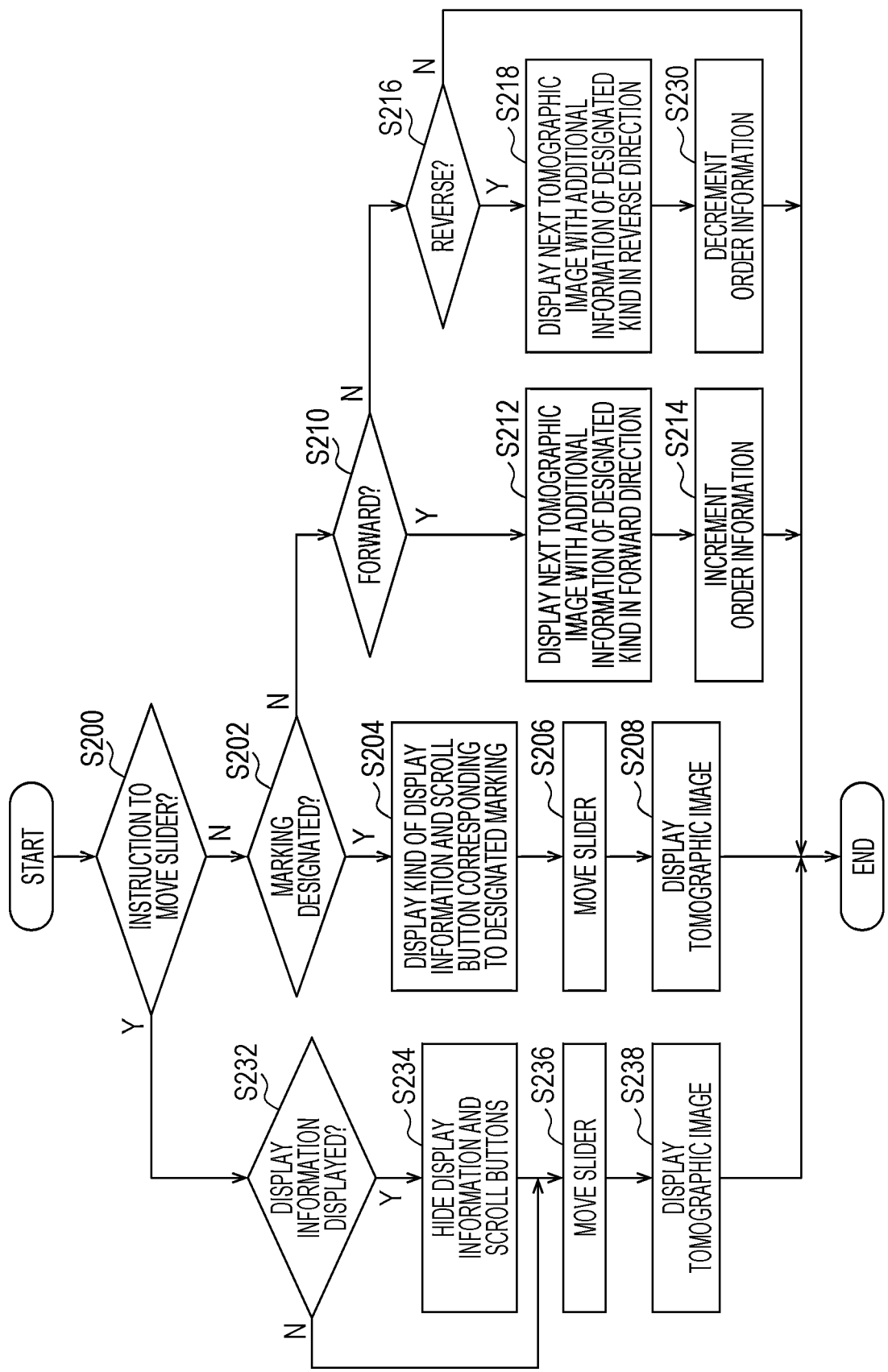
FIG. 15 is a flowchart illustrating an example of a processing routine in S16 of a display control process according to the first modification.

In step S200 in FIG. 15, the display control unit 42 determines whether or not the instruction received in step S12 above is an instruction to move the slider SD resulting from a drag operation on the slider SD, a scroll operation on the mouse wheel, or the like. If the instruction received in step S12 above is not the instruction to move the slider SD, the determination in step S200 is negative. For example, if the marking representing the additional information at the slider SD is clicked or if the scroll button B is clicked, the determination in step S200 is negative and thus the process proceeds to step S202.

In step S202, the display control unit 42 determines whether or not the instruction received in step S12 above is an instruction resulting from designation (clicking) of the marking representing the additional information at the slider SD. If the determination in step S202 is positive, the process proceeds to step S204.

In step S204, the display control unit 42 performs control to display, in the display region A2, the display information WN and the scroll buttons B corresponding to the additional information of the kind corresponding to the designated marking. For example, as described above, if the user clicks the marking CD representing the computer-added additional information, the display control unit 42 performs control to display, in the display region A2, the display information WNau as the display information WN and the scroll buttons B as illustrated in the right-side diagram of FIG. 14.

In step S206, the display control unit 42 performs control to move the slider SD to the position, on the slider bar SB, corresponding to the tomographic position according to the position of the marking designated by the user on the slider bar SB. In next step S208, the display control unit 42 performs control to switch the tomographic image in the display region A3 to the specific tomographic image at the tomographic position indicated by the slider SD. In response to the end of the processing of step S208, the processing routine illustrated in FIG. 15 ends.

On the other hand, if a negative determination is obtained in step S202 above, the process proceeds to step S210. In step S210, the display control unit 42 determines whether or not the instruction received in step S12 above is the specific display instruction received as a result of clicking of the forward button FB. If the specific display instruction resulting from clicking of the forward button FB is received, the determination in step S210 is positive and thus the process proceeds to step S212.

In step S212, the display control unit 42 performs control to display, in the display region A3, the next specific tomographic image with the additional information of the designated kind in the forward direction. For example, suppose a state in which the display information WNau and the scroll buttons B for the computer-added additional information are displayed in the display region A2 and an n-th specific tomographic image among the specific tomographic images with the computer-added additional information is displayed in the display region A3. In the case, in response to the user clicking the marking CD representing the computer-added additional information, the display control unit 42 performs control to display an (n+1)-th specific tomographic image in the display region A3. The display control unit 42 also performs control to move the slider SD to the position, on the slider bar SB, corresponding to the tomographic position of the specific tomographic image displayed in the display region A3.

If the user clicks the forward button FB in a state in which the tomographic image at the tomographic position closest to the foot side of the subject is displayed in the display region A3, there is no tomographic image of which the tomographic position is in the forward direction relative to the tomographic image currently in the display region A3. In this case, the display control unit 42 may perform control to keep displaying the tomographic image currently displayed in the display region A3 as it is. In this case, the display control unit 42 may skip this step. In such a case, the display control unit 42 preferably performs control to display, on the display 23, information indicating that there is no specific tomographic image to be displayed.

In next step S214, the display control unit 42 increments the order information of the display information WN. In response to the end of the processing of step S214, the processing routine illustrated in FIG. 15 ends.

On the other hand, if the specific display instruction resulting from clicking of the forward button FB is not received in step S210 above, that is, if the specific display instruction resulting from clicking of the reverse button RB is received, the determination is negative and thus the process proceeds to step S216.

In step S216, the display control unit 42 determines whether or not the instruction received in step S12 above is the specific display instruction received as a result of clicking of the reverse button RB. If the specific display instruction resulting from clicking of the reverse button RB is received, the determination in step S216 is positive and thus the process proceeds to step S218.

In step S218, the display control unit 42 performs control to display, in the display region A3, the next specific tomographic image with the additional information of the designated kind in the reverse direction. For example, suppose a state in which the display information WNau and the scroll buttons B for the computer-added additional information are displayed in the display region A2 and an n-th specific tomographic image among the specific tomographic images with the computer-added additional information is displayed in the display region A3. In the case, in response to the user clicking the marking CD representing the computer-added additional information, the display control unit 42 performs control to display an (n−1)-th specific tomographic image in the display region A3. The display control unit 42 also performs control to move the slider SD to the position, on the slider bar SB, corresponding to the tomographic position of the specific tomographic image displayed in the display region A3.

In response to the user clicking the reverse button RB in a state in which the tomographic image at the tomographic position closest to the head side of the subject is displayed in the display region A3, there is no tomographic image of which the tomographic position is in the reverse direction relative to the tomographic image currently in the display region A3. In this case, the display control unit 42 may perform control to keep displaying the tomographic image currently displayed in the display region A3 as it is. In this case, the display control unit 42 may skip this step. In such a case, the display control unit 42 preferably performs control to display, on the display 23, information indicating that there is no specific tomographic image to be displayed.

In next step S230, the display control unit 42 decrements the order information of the display information WN. In response to the end of the processing of step S230, the processing routine illustrated in FIG. 15 ends. If the determination in step S216 above is negative, the processing routine illustrated in FIG. 15 also ends.

On the other hand, if the received instruction is an instruction to move the slider SD resulting from a drag operation on the slider SD, a scroll operation on the mouse wheel, or the like in step S200 above, the determination is positive and thus the process proceeds to step S232.

In step S232, the display control unit 42 determines whether or not the display information WN is displayed in the display region A2. Specifically, the display control unit 42 determines whether or not the display information WN and the scroll buttons B are displayed in the display region A2. If the display information WN is not displayed in the display region A2, the determination in step S232 is negative and thus the process proceeds to step S236. On the other hand, if the display information WN is displayed in the display region A2, the determination in step S232 is positive and thus the process proceeds to step S234.

In step S234, the display control unit 42 performs control to hide the display information WN and the scroll buttons B that are displayed in the display region A2. This control results in a state in which nothing is displayed in the display region A2 as illustrated in the left-side diagram of FIG. 14.

In next step S236, the display control unit 42 performs control to move the slider SD to the position, on the slider bar SB, corresponding to the tomographic position designated through the user operation. In next step S238, the display control unit 42 performs control to switch the tomographic image in the display region A3 to the tomographic image at the designated tomographic position. In response to the end of the processing of step S238, the processing routine illustrated in FIG. 15 ends.

As described above, in the present modification, the display control unit 42 performs control to display, in the display region A2, the display information WN and the scroll buttons B corresponding to the additional information of the kind selected by the user. Thus, similarly to the embodiment described above, the display control apparatus 12 according to the present modification can make it easier to observe the specific tomographic image with the additional information.

Second Modification

In the configurations described above, the configuration has been described in which the display control unit 42 displays the display information WN and the scroll buttons B for each kind of the additional information. Specifically, FIG. 6 illustrates the configuration in which the display information WN and the scroll buttons B are displayed adjacently in combination in the display region A2 for each kind of the additional information. FIG. 14 also illustrates the configuration in which the display information WN and the scroll buttons B are displayed in combination in the display region A2 for each kind of the additional information one by one.

Figure 16:
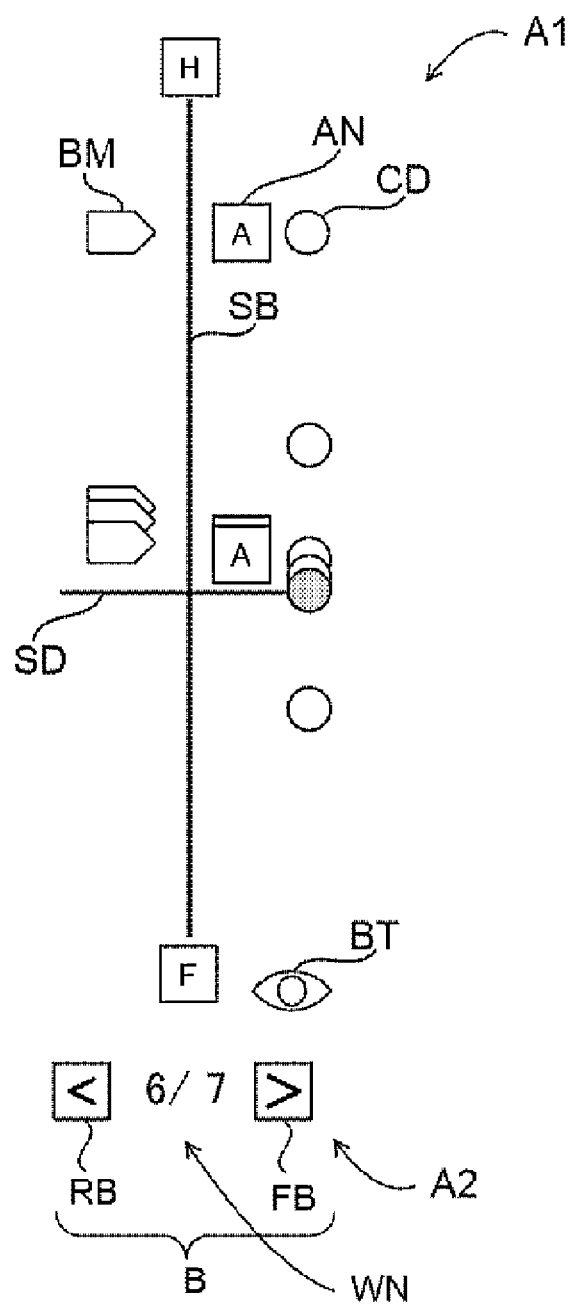
FIG. 16 is a diagram for describing display information and scroll buttons according to a second modification.

By contrast, as in the present modification illustrated in FIG. 16, a configuration may be employed in which the display information WN and the scroll button B are displayed in combination irrespective of the kinds of the additional information. The example in FIG. 16 illustrates a case where the specific tomographic image displayed in the display region A3 is an n-th specific tomographic image among m specific tomographic images with some kind of the additional information is denoted as "n/m" irrespective of the kinds.

In the example illustrated in FIG. 16, in response to the user operating the scroll button B, the display control unit 42 performs control to sequentially display only the specific tomographic images with some kind of the additional information irrespective of the kinds of the additional information. Specifically, in response to clicking of the forward button FB, the display control unit 42 performs control to display, in the display region A3, a specific tomographic image that is at the next tomographic position of the tomographic position of the specific tomographic image currently displayed in the display region A3 in the forward direction among the plurality of specific tomographic images with some kind of the additional information. In this case, the display control unit 42 moves the slider SD to the tomographic position of the specific tomographic image displayed in the display region A3 and increments the displayed order information WN as in the configuration described above. On the other hand, in response to clicking of the reverse button RB, the display control unit 42 performs control to display, in the display region A3, a specific tomographic image that is at the next tomographic position of the tomographic position of the specific tomographic image currently displayed in the display region A3 in the reverse direction among the plurality of specific tomographic images with some kinds of the additional information. In this case, the display control unit 42 moves the slider SD to the tomographic position of the specific tomographic image displayed in the display region A3 and decrements the displayed order information WN as in the configurations described above.

As described above, in the present modification, the display control unit 42 performs control to display, in the display region A2, the combination of the display information WN and the scroll buttons B corresponding to the total number of tomographic images with the additional information regardless of the kinds of the additional information. Thus, as in the configurations described above, the display control apparatus 12 of the present modification enables only the tomographic images with the additional information to be consecutively observed while skipping tomographic images without any additional information and thus can make it easier to observe the specific tomographic images with the additional information.

Note that the technique of the present disclosure is not limited by the first and second modifications described above. For example, instead of giving an instruction to forward through clicking of the forward button FB of the scroll buttons B and giving an instruction to reverse through clicking of the reverse button RB of the scroll buttons B, the user may place the cursor over the display information WN and move the mouse wheel to give the instruction to forward or the instruction to reverse according to the direction of the movement.

Figure 17:
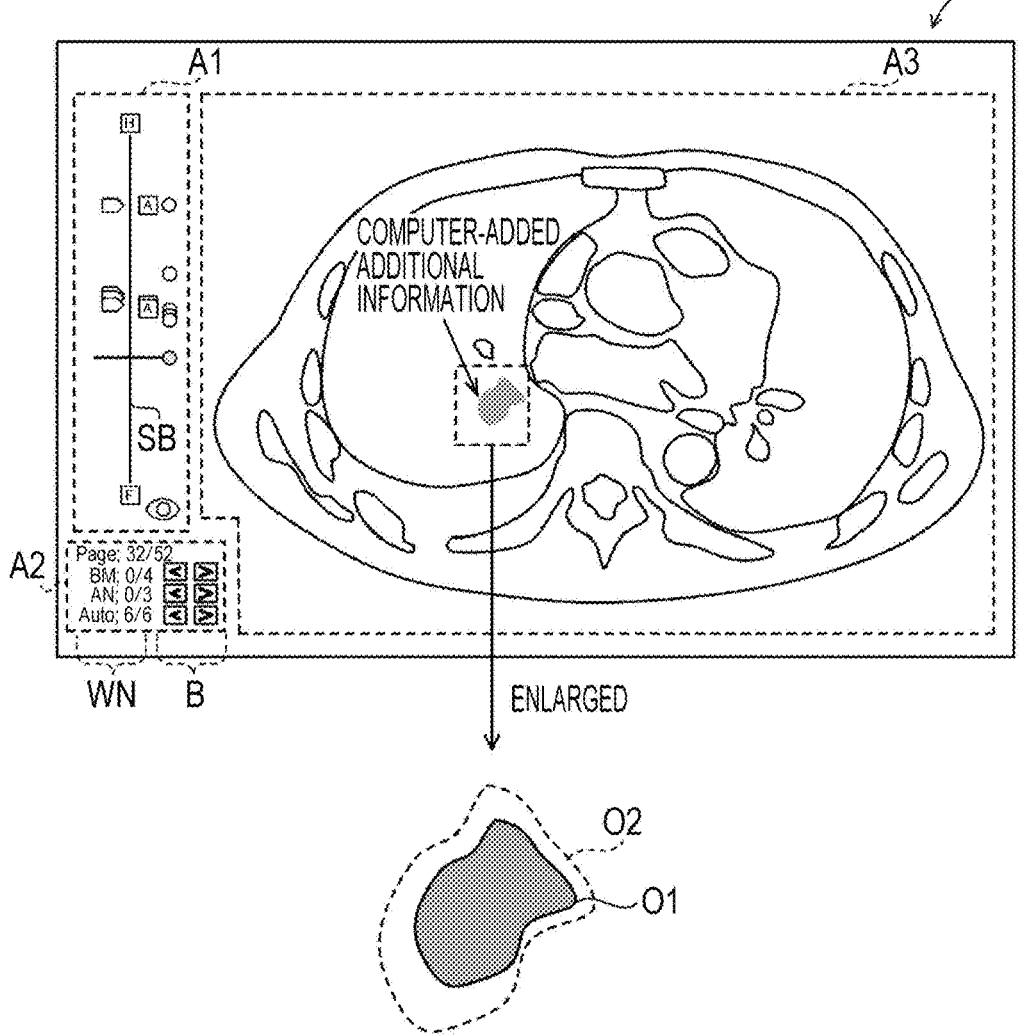
FIG. 17 is a diagram illustrating an example of a display state of computer-added additional information according to a modification.

In the embodiment described above, for a tomographic image with the computer-added additional information, the display control unit 42 may perform control to further display, in addition to an outline O1 of a region of interest represented by the computer-added additional information added to the tomographic image, an outline O2 of the region of interest as illustrated in FIG. 17. In this case, for example, the display control unit 42 performs control to display, as the outline O2, an outline of the region of interest represented by the computer-added additional information added to any of the other tomographic images in which the same region of interest is detected. Specifically, the display control unit 42 performs control to display, as the outline O2, the largest outline among outlines of the region of interest represented by the computer-added additional information added to some of the other tomographic images in which the same region of interest is detected. Examples of the largest outline used herein include an outline for the largest area and an outline with the longest length.

Figure 18:
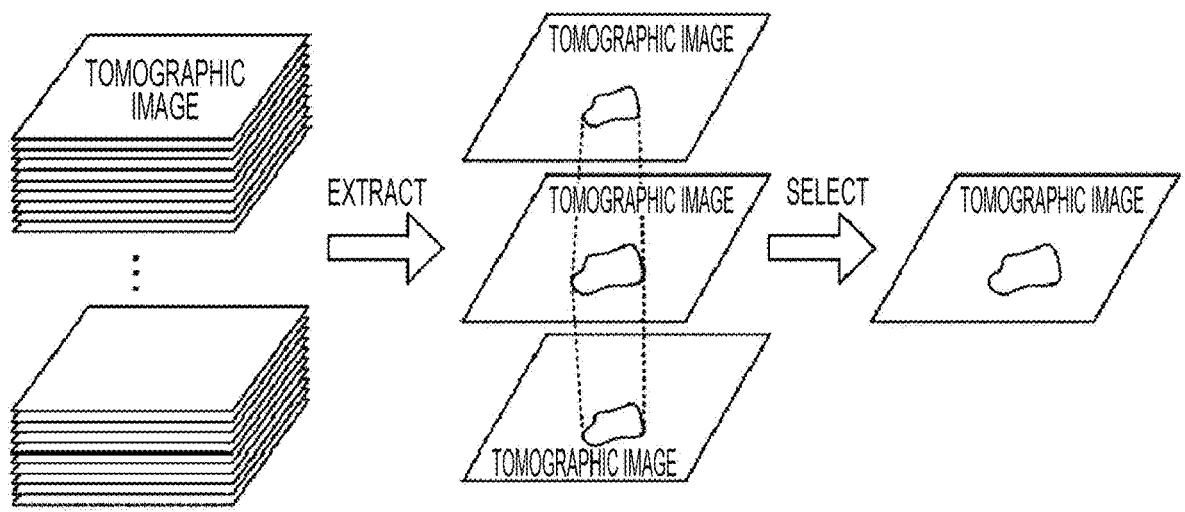
FIG. 18 is a diagram for describing a process of adding computer-added additional information according to a modification.

In the embodiment described above, the case has been described where the computer adds the computer-added additional information to all the tomographic images in which the region of interest is detected. However, the configuration is not limited to this. As illustrated in FIG. 18, the computer may extract a group of tomographic images that includes the same target (region of interest, for example) from a plurality of tomographic images constituting a three-dimensional medical image, select a representative tomographic image from the extracted group of tomographic images, and add the computer-added additional information only to the selected tomographic image. In this case, for example, the computer identifies, as the same region of interest, regions of interest for which an absolute value of a difference between barycentric positions of the regions of interest detected in consecutive tomographic images is less than or equal to a predetermined first threshold value and an absolute value of a difference between areas of the regions of interest is less than or equal to a predetermined second threshold value. In this case, values set in advance as upper-limit values of the respective differences of the same region of interest between consecutive tomographic images can be used as the first threshold value and the second threshold value. In this case, for example, the computer extracts, as the representative tomographic image, a tomographic image in which a region of interest having the largest area or the longest outline length is detected from the extracted group of tomographic images. The computer in this case may be the display control apparatus 12, a control device included in the imaging apparatus 14, the image storage apparatus 16, or a computer external to the diagnosis assistance system 10.

The processing performed by the computer to select the tomographic image to which the additional information is to be added in this case may be performed in the same manner by the user via the input unit 24. The user-added additional information in this case is information added by the user to the representative tomographic image of the group of tomographic images including the same target among the plurality of tomographic images.

Figure 19:
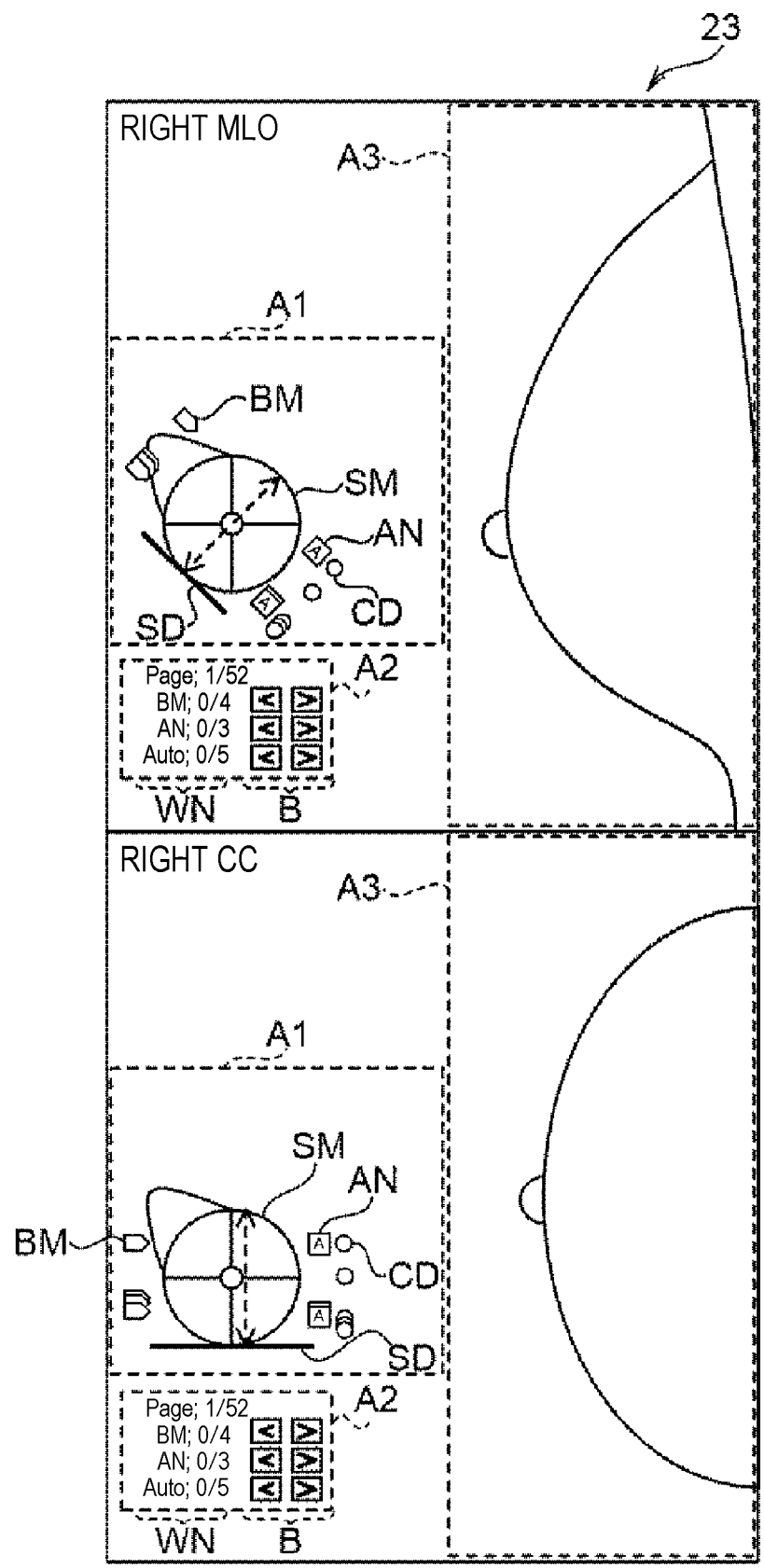
FIG. 19 is a diagram illustrating an example of a screen displaying a schema and a tomographic image according to a modification.

In the embodiment described above, the case has been described where the slider bar SB and the slider SD are used as a designation object for designating a tomographic position corresponding to each of a plurality of tomographic images. However, the designation object is not limited to this. For example, as illustrated in FIG. 19, a schema SM and the slider SD may be used as the designation object for designating a tomographic position corresponding to each of a plurality of tomographic images. The schema SM used herein means a schematic diagram schematically illustrating a part of a human body. FIG. 19 illustrates an example in which a plurality of tomographic images for medical use obtained through tomosynthesis imaging using a mammography apparatus are used as the plurality of tomographic images. The upper part of FIG. 19 illustrates a tomographic image obtained by performing medio-lateral oblique (MLO) imaging on the right breast, and the lower part of FIG. 19 illustrates a tomographic image obtained by performing cranio-caudal (CC) imaging on the right breast. In FIG. 19, the depth direction of the tomographic images, that is, the moving direction of the slider SD is indicated by a double-headed dash arrow. For example, the user drags the slider SD to the tomographic position, on the schema SM, of the tomographic image which the user desires to display to designate the tomographic position also in this configuration example. In this case, when the additional information is added to the tomographic image corresponding to the designated tomographic position, the marking indicating the additional information is displayed in an emphasized manner. In this case, a specific display instruction to display, among the plurality of tomographic images, only the specific tomographic images that are on either side in the depth direction of the schema SM with respect to a reference that is the current position designated on the schema SM is received. In response to receipt of the specific display instruction, only the specific tomographic images are displayed in an order according to the depth direction. In response to only the specific tomographic images being displayed in the order according to the depth direction, the markings representing the additional information added to the respective specific tomographic images are displayed in an emphasized manner in the order according to the depth direction. In this configuration example, the markings AN and CD may be displayed in the schema SM so that the two-dimensional arrangement when the breast is viewed from the front can be understood.

Both the slider SD and the slider bar SB illustrated in FIGS. 4 and 5 and the schema SM and the slider SD illustrated in FIG. 19 may be displayed in the display region A1. In this configuration example, an operation performed on either one of these may be reflected in the other.

In the embodiment described above, for example, various processors mentioned below can be used as a hardware structure of processing units such as the reception unit 40 and the display control unit 42 that perform various processes. The aforementioned various processors include, in addition to a CPU which is a general-purpose processor that executes software (program) to function as the various processing units as described above, a programmable logic device (PLD), such as a field programmable gate array (FPGA), which is a processor whose circuitry is changeable after production; a dedicated electric circuit, such as an application specific integrated circuit (ASIC), which is a processor having circuitry designed exclusively for executing specific processing; and the like.

A single processing unit may be constituted by one of these various processors, or by a combination of two or more processors of the same kind or different kinds (for example, a combination of a plurality of FPGAs or a combination of a CPU and an FPGA). In addition, a plurality of processing units may be constituted by a single processor.

Examples in which the plurality of processing units are constituted by a single processor include a first configuration, as exemplified by computers such as a server and a client, in which a combination of one or more CPUs and software constitutes the single processor and this processor functions as the plurality of processing units. The examples also include a second configuration, as exemplified by a System On Chip (SoC) or the like, in which the processor that implements functions of the entire system including the plurality of processing units on a single integrated circuit (IC) chip is used. As described above, the various processing units are constituted using one or more of the various processors above in terms of the hardware structure.

More specifically, electric circuitry in which circuit elements such as semiconductor elements are combined can be used in terms of the hardware structure of these various processors.

In the embodiment above, the configuration has been described in which the display control program 30 is stored (installed) in the storage unit 22 in advance. However, the configuration is not limited to this. The display control program 30 may be provided in a form of a recording medium, such as a compact disc read-only memory (CD-ROM), a digital versatile disc read-only memory (DVD-ROM), or a Universal Serial Bus (USB) memory, on which the display control program 30 is recorded. The display control program 30 may also be downloaded from an external apparatus via a network.

In addition, the configurations of the diagnosis assistance system 10, the display control apparatus 12, and the like; the display control method; and the like described in the embodiment and modifications above are merely an example. Thus, it is needless to say that the configurations, the method, and the like can be changed in accordance with a circumstance within a scope not departing from the gist of the present invention.

The disclosure of JP2020-040358 filed Mar. 9, 2020 is incorporated herein by reference in its entirety.

All the documents, patent applications, and technical standards mentioned in this specification are incorporated herein by reference to the same extent as if the individual documents, patent applications, and technical standards were specifically and individually described to be incorporated by reference.

What is claimed is:

1. A display control apparatus comprising
at least one processor that performs control to:
  display a designation object for designating a tomographic position corresponding to each of a plurality of tomographic images for medical use obtained through imaging of a subject;
  display a tomographic image corresponding to a tomographic position designated by the designation object;
  display, for each of one or more specific tomographic images with additional information that is set to be added on a tomographic-image by tomographic-image basis, a marking representing the additional information at a position corresponding to a tomographic position of the specific tomographic image in a depth direction of the designation object;
  receive a specific display instruction to display, among the plurality of tomographic images, only the specific tomographic images that are on either side of the designation object in the depth direction with respect to a reference that is a current position designated by the designation object;

display, in response to receipt of the specific display instruction, only the specific tomographic images in an order according to the depth direction; and display, in response to only the specific tomographic images being displayed in the order according to the depth direction, the markings representing the additional information added to the respective specific tomographic images in an emphasized manner in the order according to the depth direction, wherein the additional information includes an outline of a region of interest in the tomographic image, and the processor performs control to display, in a case where the outline of the region of interest is added to the tomographic image corresponding to the designated tomographic position, the outline of the region of interest over the tomographic image, and performs control to further display a largest outline among outlines of the region of interest added to other tomographic images in which a region of interest identical to the region of interest being displayed is detected.

2. The display control apparatus according to claim 1, wherein the designation object includes a slider bar.

3. The display control apparatus according to claim 1, wherein the designation object includes a schema.

4. The display control apparatus according to claim 1, wherein the additional information includes a plurality of kinds of additional information, and the processor is capable of receiving, as the specific display instruction, a specific display instruction including designation of a kind of the additional information, and performs control to display, in response to receipt of the specific display instruction in which the kind of the additional information is designated, only the specific tomographic images with the additional information of the designated kind in the order according to the depth direction.

5. The display control apparatus according to claim 4, wherein the plurality of kinds include at least one of user-added additional information added by a user or computer-added additional information added by a computer.

6. The display control apparatus according to claim 4, wherein the processor is capable of receiving, as the specific display instruction, a specific display instruction not including designation of a kind of the additional information, and performs control to display, in response to receipt of the specific display instruction, all the specific tomographic images with the additional information in the order according to the depth direction irrespective of the kinds.

7. The display control apparatus according to claim 1, wherein the order according to the depth direction includes a first order corresponding to a forward direction set in advance in the depth direction and a second order corresponding to a reverse direction opposite to the forward direction, and the processor is capable of receiving, as the specific display instruction, a specific display instruction in which either the first order or the second order is designated.

8. The display control apparatus according to claim 1, wherein the processor performs control to display an instruction button for giving the specific display instruction.

9. The display control apparatus according to claim 1, wherein the processor receives the specific display instruction input by an instruction input device.

10. The display control apparatus according to claim 1, wherein the processor performs control to display the total number of specific tomographic images at a position different from a position of the designation object.

11. The display control apparatus according to claim 1, wherein the processor performs control to display the total number of specific tomographic images included in the plurality of tomographic images and order information indicating what number, in the order according to the depth direction, one of the specific tomographic images that is currently displayed based on the specific display instruction is.

12. The display control apparatus according to claim 11, wherein the additional information includes a plurality of kinds of additional information, and the processor performs control to display the total number and the order information for each of the plurality of kinds.

13. The display control apparatus according to claim 12, wherein the processor is capable of receiving, as the specific display instruction, a specific display instruction including designation of a kind of the additional information, and performs control to selectively display the total number and the order information in accordance with the designated kind.

14. The display control apparatus according to claim 1, wherein the additional information includes computer-added additional information added by a computer, and the processor receives an input for switching between displaying and hiding of the computer-added additional information, and performs control to switch between displaying and hiding of a marking representing the computer-added additional information in accordance with the received input.

15. The display control apparatus according to claim 14, wherein the processor performs control to display, for a tomographic image with the computer-added additional information, the computer-added additional information over the tomographic image, and performs control to switch between displaying and hiding of both the marking representing the computer-added additional information and the computer-added additional information over the tomographic image in accordance with the received input.

16. A display control method in which a processor, which a display control apparatus comprises, performs a process of performing control to:

display a designation object for designating a tomographic position corresponding to each of a plurality of tomographic images for medical use obtained through imaging of a subject;

display a tomographic image corresponding to a tomographic position designated by the designation object;

display, for each of one or more specific tomographic images with additional information that is set to be added on a tomographic-image by tomographic-image basis, a marking representing the additional information at a position corresponding to a tomographic position of the specific tomographic image in a depth direction of the designation object;

receive a specific display instruction to display, among the plurality of tomographic images, only the specific tomographic images that are on either side of the designation object in the depth direction with respect to a reference that is a current position designated by the designation object;

display, in response to receipt of the specific display instruction, only the specific tomographic images in an order according to the depth direction; and display, in response to only the specific tomographic images being displayed in the order according to the depth direction, the markings representing the additional information added to the respective specific tomographic images in an emphasized manner in the order according to the depth direction, wherein the additional information includes an outline of a region of interest in the tomographic image, and the processor performs control to display, in a case where the outline of the region of interest is added to the tomographic image corresponding to the designated tomographic position, the outline of the region of interest over the tomographic image, and performs control to further display a largest outline among outlines of the region of interest added to other tomographic images in which a region of interest identical to the region of interest being displayed is detected.

17. A non-transitory computer-readable storage medium storing a display control program for causing a processor, which a display control apparatus comprises, to perform a process for performing control to:

display a designation object for designating a tomographic position corresponding to each of a plurality of tomographic images for medical use obtained through imaging of a subject;

display a tomographic image corresponding to a tomographic position designated by the designation object;

display, for each of one or more specific tomographic images with additional information that is set to be added on a tomographic-image by tomographic-image basis, a marking representing the additional information at a position corresponding to a tomographic position of the specific tomographic image in a depth direction of the designation object;

receive a specific display instruction to display, among the plurality of tomographic images, only the specific tomographic images that are on either side of the designation object in the depth direction with respect to a reference that is a current position designated by the designation object;

display, in response to receipt of the specific display instruction, only the specific tomographic images in an order according to the depth direction; and display, in response to only the specific tomographic images being displayed in the order according to the depth direction, the markings representing the additional information added to the respective specific tomographic images in an emphasized manner in the order according to the depth direction, wherein the additional information includes an outline of a region of interest in the tomographic image, and the processor performs control to display, in a case where the outline of the region of interest is added to the tomographic image corresponding to the designated tomographic position, the outline of the region of interest over the tomographic image, and performs control to further display a largest outline among outlines of the region of interest added to other tomographic images in which a region of interest identical to the region of interest being displayed is detected.

* * * * *